United States Patent
Hashimoto et al.

(10) Patent No.: US 11,071,461 B2
(45) Date of Patent: Jul. 27, 2021

(54) PHOTOACOUSTIC MEASUREMENT DEVICE AND METHOD

(71) Applicant: FUJIFILM Corporation, Tokyo (JP)

(72) Inventors: Atsushi Hashimoto, Kanagawa (JP); Atsushi Osawa, Kanagawa (JP); Kaku Irisawa, Kanagawa (JP); Keiji Tsubota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 797 days.

(21) Appl. No.: 15/920,697

(22) Filed: Mar. 14, 2018

(65) Prior Publication Data

US 2018/0199821 A1 Jul. 19, 2018

Related U.S. Application Data

(63) Continuation of application No. PCT/JP2016/004308, filed on Sep. 21, 2016.

(30) Foreign Application Priority Data

Sep. 29, 2015 (JP) .............................. JP2015-190738

(51) Int. Cl.
*A61B 5/00* (2006.01)
*A61B 8/00* (2006.01)
(Continued)

(52) U.S. Cl.
CPC .......... *A61B 5/0095* (2013.01); *A61B 5/7225* (2013.01); *A61B 8/14* (2013.01);
(Continued)

(58) Field of Classification Search
CPC ....... A61B 5/0095; A61B 8/54; A61B 8/4416; A61B 5/7225; A61B 8/14; A61B 8/5207;
(Continued)

(56) References Cited

U.S. PATENT DOCUMENTS

2008/0015437 A1* 1/2008 Hongou .............. G01S 15/8927
600/443
2010/0043526 A1* 2/2010 Helwegen ............ G01N 29/022
73/24.02
(Continued)

FOREIGN PATENT DOCUMENTS

JP 6-296610 A 10/1994
JP 2014-39801 A 3/2014
(Continued)

OTHER PUBLICATIONS

International Preliminary Report on Patentability and Written Opinion of the International Searching Authority(Forms PCT/IB/326, PCT/IB/373, and PCT/ISA/237) dated Apr. 12, 2018, for International Application No. PCT/JP2016/004308, with an English Translation of the Written Opinion.
(Continued)

*Primary Examiner* — Carolyn A Pehlke
*Assistant Examiner* — Victoria Fang
(74) *Attorney, Agent, or Firm* — Birch, Stewart, Kolasch & Birch, LLP

(57) ABSTRACT

An acoustic wave detector detects photoacoustic waves generated by absorbing measurement light emitted toward a subject, and reflected acoustic waves with respect to acoustic waves transmitted toward the subject. A preamplifier amplifies a detection signal output by the acoustic wave detector. A bypass unit is intended to output the detection signal without passing through the preamplifier. Controller causes the preamplifier to enter an operating state and selects a first path along which the detection signal is amplified by the preamplifier and then is input to the reception circuit as a signal path in a case where the photoacoustic waves are detected. The controller stops an amplification operation in the preamplifier and selects a second path along which the detection signal is input to the reception circuit via a bypass
(Continued)

unit as the signal path in a case where reflected acoustic waves are detected.

16 Claims, 12 Drawing Sheets

(51) Int. Cl.
*A61B 8/14* (2006.01)
*G01S 7/52* (2006.01)
*A61B 8/08* (2006.01)

(52) U.S. Cl.
CPC .......... *A61B 8/4416* (2013.01); *A61B 8/5207* (2013.01); *A61B 8/54* (2013.01); *A61B 8/5261* (2013.01); *A61B 8/56* (2013.01); *G01S 7/52096* (2013.01)

(58) Field of Classification Search
CPC ................ A61B 8/5261; A61B 5/0097; G01N 21/1702; G01N 29/2418; G01S 15/8965; G01S 15/8968; G01S 7/52017–52098; G02F 1/33; G10K 15/046

USPC ........................................................ 600/443
See application file for complete search history.

(56) References Cited

U.S. PATENT DOCUMENTS

| 2014/0251017 A1* | 9/2014 | Kandori | G01N 29/2418 |
| | | | 73/661 |
| 2018/0364343 A1* | 12/2018 | Bai | G01S 7/52028 |

FOREIGN PATENT DOCUMENTS

| JP | 2014-198234 A | 10/2014 | |
| JP | 2014-213158 A | 11/2014 | |
| JP | 2014213158 A | * 11/2014 | ........... A61B 6/4417 |

OTHER PUBLICATIONS

International Search Report (Form PCT/ISA/210), dated (Dec. 20, 2016, for International Application No. PCT/JP2016/004308, with English Translation.

* cited by examiner

PHOTOACOUSTIC MEASUREMENT DEVICE AND METHOD

CROSS-REFERENCE TO RELATED APPLICATIONS

This application is a continuation application of International Application No. PCT/JP2016/004308 filed Sep. 21, 2016, the disclosure of which is incorporated herein by reference in its entirety. Further, this application claims priority from Japanese Patent Application No. 2015-190738, filed Sep. 29, 2015, the disclosure of which is incorporated herein by reference in its entirety.

BACKGROUND OF THE INVENTION

1. Field of the Invention

The present invention relates to a photoacoustic measurement device and method, and more particularly to, a photoacoustic measurement device and a method of detecting photoacoustic waves generated by a light absorber absorbing light.

2. Description of the Related Art

An ultrasonic inspection method is known as a type of image inspection method capable of non-invasively inspecting a state of the inside of a living body. In ultrasonic examination, an ultrasonic probe capable of transmitting and receiving ultrasonic waves is used. In a case where ultrasonic waves are transmitted from the ultrasonic probe to a subject (living body), the ultrasonic waves travel inside the living body and are reflected at a tissue interface. A state of the inside can be imaged by receiving the reflected ultrasonic waves using the ultrasonic probe and calculating a distance on the basis of a time until the reflected ultrasonic wave returns to the ultrasonic probe.

Further, photoacoustic imaging for imaging the inside of the living body using a photoacoustic effect is known. Generally, in photoacoustic imaging, for example, pulsed laser light is radiated to the inside of the living body as measurement light. In the inside of the living body, the biological tissue absorbs energy of the pulsed laser light, and ultrasonic waves (photoacoustic waves) are generated by adiabatic expansion due to the energy. By detecting the photoacoustic waves using an ultrasonic probe or the like and constructing a photoacoustic image on the basis of the detection signal, visualization of the inside of the living body based on the photoacoustic waves is possible.

A photoacoustic measurement probe that radiates measurement light toward a subject and measures photoacoustic waves generated in the subject due to absorption of the light is known. The photoacoustic measurement probe is often capable of transmitting and receiving ultrasonic waves. Generally, photoacoustic waves are weaker than reflected ultrasonic waves, and a detection signal thereof is weak. A photoacoustic measurement probe including a preamplifier built thereinto in order to amplify the weak detection signal is known (for example, JP2014-39801A).

Incidentally, in a case where an ultrasonic vibrator in the probe is driven to transmit the ultrasonic waves to the subject, the ultrasonic vibrator generates heat. In a case where the preamplifier amplifies the detection signal, the preamplifier correspondingly generates heat. Therefore, in the case of the probe including the preamplifier built thereinto, a new heat generation source called the preamplifier is generated in addition to the ultrasonic vibrator. In the probe including the preamplifier built thereinto, an increase in temperature of the probe due to the heat sources and, particularly, an increase in temperature of a portion of a probe surface in contact with a human body becomes a problem. Since a photoacoustic probe is used in contact with a human body, it is necessary to suppress a surface temperature of the probe to a certain temperature or less (for example, 43° C. or less).

Since the suppression of heat generation in the ultrasonic vibrator is a trade-off with image quality of an ultrasonic image, it is preferable to suppress heat generation in the preamplifier in order to suppress the increase in temperature without sacrificing the image quality. In connection with such a problem, JP2014-198234A describes that a detection operation is not performed in a detection circuit including a preamplifier in a period in which a detector element of a probe does not receive acoustic waves. In JP2014-198234A, heat generation of the preamplifier in a period in which the detector element does not receive the acoustic wave can be suppressed by operating the detection circuit only in the period in which the detector element receives the acoustic waves. [0008] However, in JP2014-198234A, for example, in a case where transmission and reception of ultrasonic waves and detection of photoacoustic waves are alternately performed, a period in which the preamplifier is not operated is only about half of the whole period. Therefore, there is a problem in that suppression of an increase in surface temperature is not sufficient.

SUMMARY OF THE INVENTION

In view of the above circumstances, an object of the present invention is to provide photoacoustic measurement device and method that enable heat generation in a probe including a preamplifier to be further suppressed in a case where the probe is used.

In order to achieve the above object, the present invention provides a photoacoustic measurement device comprising: a probe including an acoustic wave detector that detects photoacoustic waves generated by a light absorber in a subject absorbing measurement light emitted toward the subject and reflected acoustic waves with respect to acoustic waves transmitted toward the subject and outputs a detection signal, a preamplifier that amplifies the detection signal output by the acoustic wave detector, and a bypass unit that outputs the detection signal without passing through the preamplifier; a reception circuit that receives the detection signal amplified by the preamplifier or the detection signal output by the bypass unit; and controller for causing the preamplifier to enter an operating state and selecting a first path along which the detection signal is amplified by the preamplifier and then is input to the reception circuit as a signal path between the acoustic wave detector and the reception circuit in a case where the photoacoustic waves are detected by the acoustic wave detector, and for stopping an amplification operation in the preamplifier and selecting a second path along which the detection signal is input to the reception circuit through the bypass unit as the signal path in a case where the reflected acoustic waves are detected by the acoustic wave detector.

The present invention also provides a photoacoustic measurement method using a probe including an acoustic wave detector that detects photoacoustic waves generated by absorbing measurement light emitted toward a subject and reflected acoustic waves with respect to acoustic waves transmitted toward the subject and outputs a detection signal, and a preamplifier that amplifies the detection signal output by the acoustic wave detector, the method comprising: causing the preamplifier to enter an operating state and selecting a first path along which the detection signal is amplified by the preamplifier and then is input to a reception circuit that receives the detection signal as a signal path between the acoustic wave detector and the reception circuit in a case where the photoacoustic waves are detected; and stopping an amplification operation in the preamplifier and selecting a second path along which the detection signal is input to the reception circuit without passing through the preamplifier as the signal path in a case where the reflected acoustic waves are detected.

DESCRIPTION OF THE PREFERRED EMBODIMENTS

Figure 1:
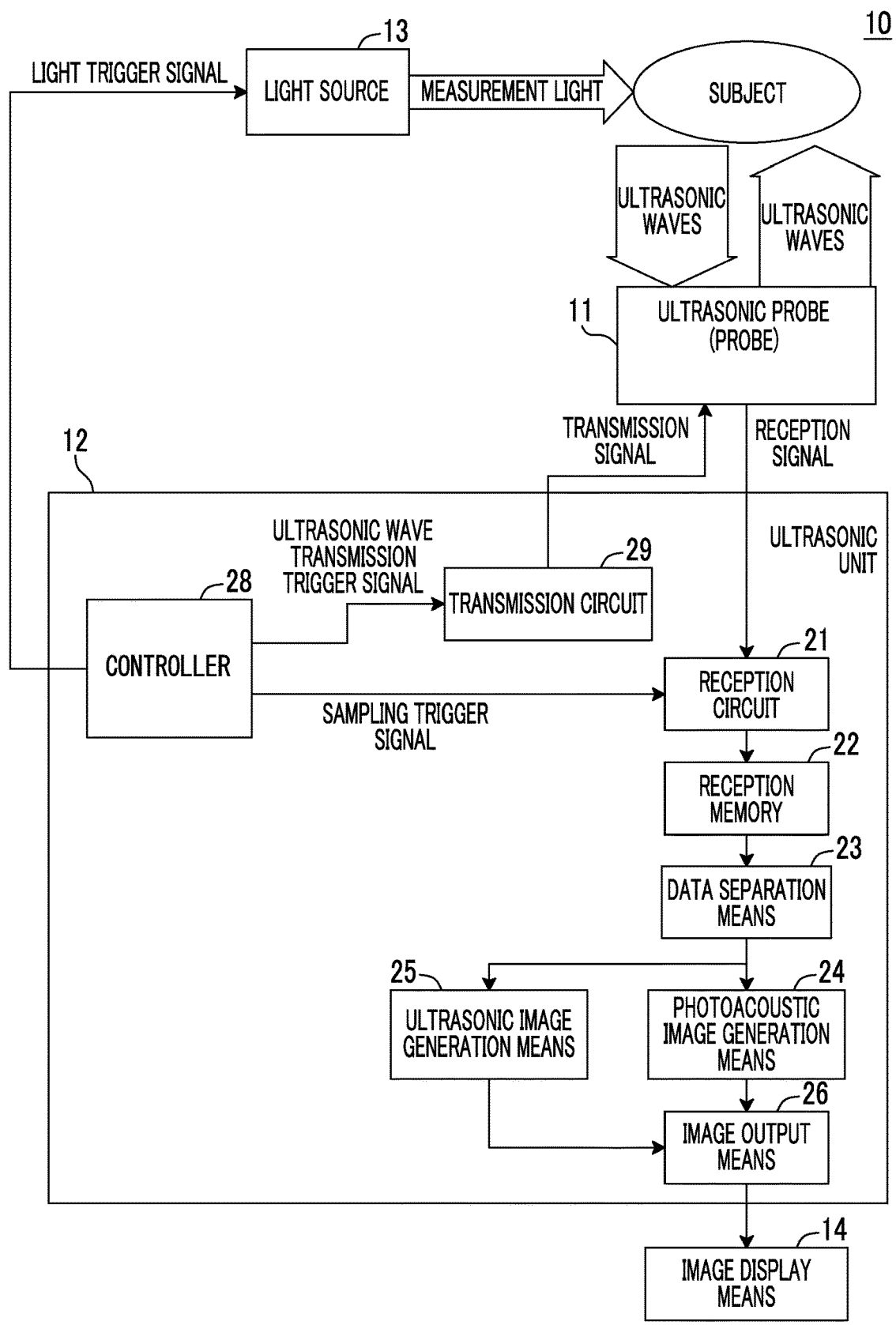
FIG. 1 is a block diagram illustrating a photoacoustic measurement device according to a first embodiment of the present invention.

Hereinafter, embodiments of the present invention will be described in detail with reference to the drawings. FIG. 1 illustrates a photoacoustic measurement device according to a first embodiment of the present invention. The photoacoustic measurement device 10 includes a probe (ultrasonic probe) 11, an ultrasonic unit 12, and a light source 13. In the embodiment of the present invention, ultrasonic waves are used as acoustic waves, but the acoustic waves are not limited to the ultrasonic waves, and acoustic waves at an audible frequency may be used as long as an appropriate frequency may be selected according to an inspection target and/or measurement conditions.

The light source 13 emits measurement light with which a subject such as a biological tissue is irradiated. A wavelength of the measurement light is appropriately set according to a biological tissue of an observation target or the like. The light source 13 is, for example, a solid laser light source. A type of the light source is not particularly limited, and the light source 13 may be a laser diode light source (semiconductor laser light source), or may be a light amplification type laser light source using a laser diode light source as a seed light source. A light source other than the laser light source may be used. The measurement light emitted from the light source 13 is guided to a probe 11 using light guiding means such as an optical fiber, and is radiated from the probe 11 toward the subject. An irradiation position of the measurement light is not particularly limited, and irradiation of the measurement light may be performed from a place other than the probe 11.

The probe 11 detects the photoacoustic waves generated by absorbing the measurement light emitted from the light absorber in the subject toward the subject. In addition to the detection of the photoacoustic waves, the probe 11 performs transmission of acoustic waves (ultrasonic waves) to the subject and reception of reflected ultrasonic waves (reflected ultrasonic waves) with respect to the transmitted ultrasonic waves. Transmission and reception of sound waves may be performed at separate positions. For example, transmission of the ultrasonic waves from a position different from the probe 11 is performed, and reflected ultrasonic waves with respect to the transmitted ultrasonic waves may be received by the probe 11. The type of the probe 11 is not particularly limited, and the probe 11 may be a linear probe or may be a convex probe or a sector probe.

The ultrasonic unit 12 includes a reception circuit 21, a reception memory 22, data separation means 23, photoacoustic image generation means 24, ultrasonic image generation means 25, image output means 26, controller 28, and a transmission circuit 29. The ultrasonic unit 12 constitutes a signal processing device. The ultrasonic unit 12 is configured as a computer device including, for example, a processor, a memory, and a bus. A program relating to photoacoustic image generation is incorporated in the ultrasonic unit 12, and at least some of functions of each unit in the ultrasonic unit 12 is realized by an operation of the program.

The reception circuit 21 receives the detection signal that is output by the probe 11 and stores the received detection signal in the reception memory 22. The reception circuit 21 typically includes a low noise amplifier, a variable gain amplifier, a low pass filter, and an analog to digital converter (AD converter). The detection signal of the probe 11 is amplified in the low noise amplifier and then gain-adjusted according to a depth in the variable gain amplifier. A high frequency component is cut in the low pass filter, stored in a digital signal in the AD converter, and stored in the memory 22. The reception circuit 21 is configured as, for example, one integrated circuit (IC).

The probe 11 outputs the detection signal of the photoacoustic waves and the detection signal of the reflected ultrasonic waves, and the reception memory 22 stores detection signals (sampling data) of the photoacoustic waves and the reflected ultrasonic waves subjected to AD conversion. The data separation means 23 reads the sampling data of the detection signal of the photoacoustic waves from the reception memory 22 and transmits the sampling data to the photoacoustic image generation means 24. Further, the data separation means 23 reads the sampling data of the reflected ultrasonic waves from the reception memory 22 and transmits the sampling data to the ultrasonic image generation means (reflected acoustic wave image generation means) 25.

The photoacoustic image generation means 24 generates a photoacoustic image on the basis of the detection signal of the photoacoustic waves detected by the probe 11. The generation of the photoacoustic image includes, for example, image reconstruction such as phase matching addition, wave detection, and logarithmic transformation. The ultrasonic image generation means 25 generates an ultrasonic image (reflected acoustic wave image) on the basis of the detection signal of the reflected ultrasonic wave detected by the probe 11. The generation of the ultrasonic image also includes image reconstruction such as phase matching addition, wave detection, and logarithmic transformation. The image output means 26 outputs the photoacoustic image and the ultrasonic image to the image display means 14 such as a display device.

The controller 28 controls each unit in the ultrasonic unit 12. For example, in a case where the photoacoustic image is acquired, the controller 28 transmits a light trigger signal to the light source 13 and causes the light source 13 to emit the measurement light. Further, according to the emission of the measurement light, the controller 28 transmits a sampling trigger signal to the reception circuit 21 to control, for example, a sampling start timing of the photoacoustic waves.

In a case where the ultrasonic image is acquired, the controller 28 transmits an ultrasonic transmission trigger signal to the transmission circuit 29 to instruct the transmission circuit 29 to transmit the ultrasonic waves. In a case where the transmission circuit 29 receives the ultrasonic transmission trigger signal, the transmission circuit 29 outputs, to the probe 11, a transmission signal for transmitting the ultrasonic waves from the probe 11 to causes the probe 11 to transmit the ultrasonic waves. The probe 11, for example, scans an acoustic line while shifting the acoustic line by one line to perform detection of the reflected ultrasonic waves. The controller 28 transmits the sampling trigger signal to the reception circuit 21 according to an ultrasonic wave transmission timing to cause the sampling of the reflected ultrasonic waves to start.

Figure 2:
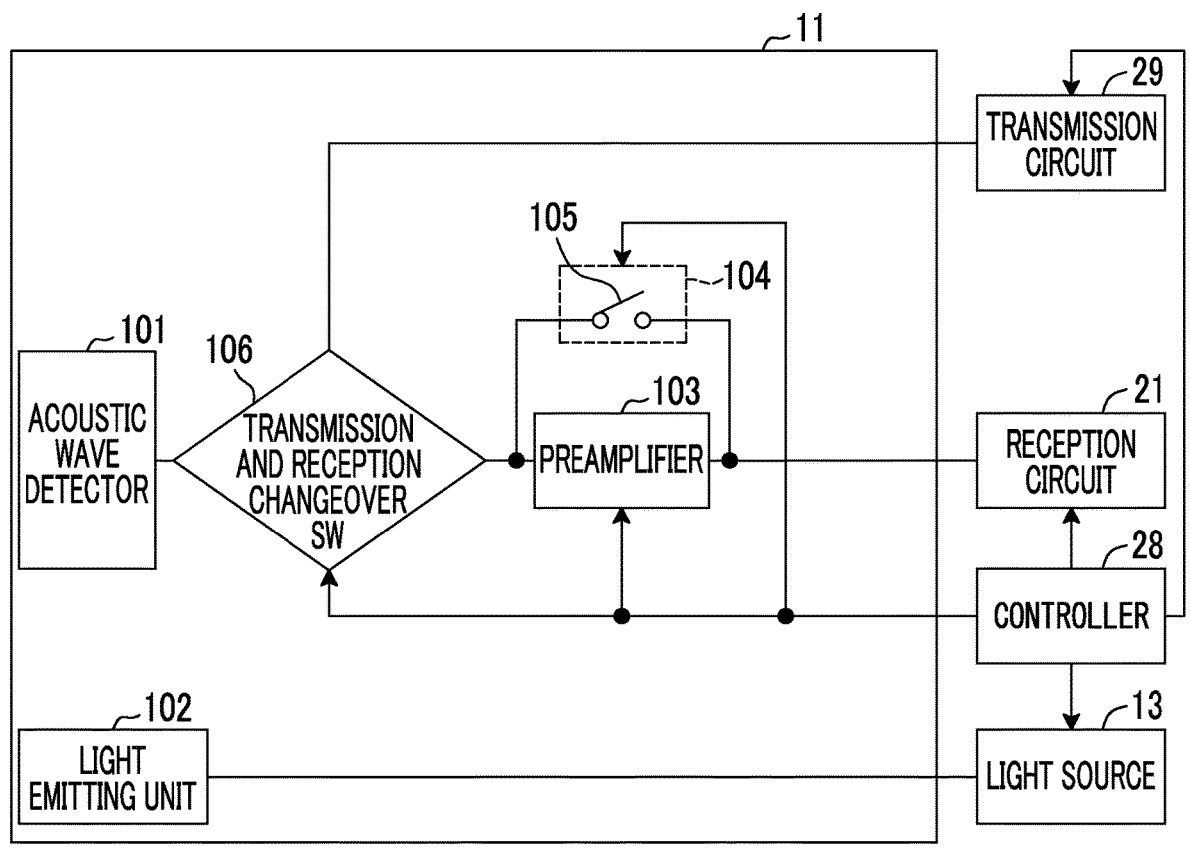
FIG. 2 is a block diagram illustrating a configuration of a probe.

FIG. 2 illustrates a configuration of the probe 11. The probe 11 includes an acoustic wave detector 101, a light emitting unit 102, a preamplifier 103, a bypass unit 104, and a transmission and reception changeover switch 106. The light emitting unit 102 emits the measurement light output from the light source 13 toward the subject. The light source 13 and the light emitting unit 102 are connected to each other by, for example, a bundle fiber or the like. The light emitting unit 102 includes, for example, a light guide plate that guides the measurement light, and/or a diffusion plate that diffuses the measurement light. A light emitting end of the optical fiber may be used as the light emitting unit 102.

The acoustic wave detector 101 includes, for example, a plurality of detector elements (ultrasonic vibrators) arranged one-dimensionally. The acoustic wave detector 101 detects the photoacoustic waves and the reflected ultrasonic waves and outputs a detection signal. The acoustic wave detector 101 also serves as an acoustic wave transmitter that performs transmission of the acoustic waves to the subject. The transmission and reception changeover switch 106 switches a connection destination of the acoustic wave detector 101 between the preamplifier 103 (an input node thereof) and the transmission circuit 29 (an output node thereof) arranged in the ultrasonic unit 12 (see FIG. 1).

The preamplifier 103 receives the detection signal output from the acoustic wave detector 101 via the transmission and reception changeover switch 106, and amplifies the detection signal. The preamplifier 103 can switch an operating state between an operating state in which amplification of the detection signal is performed and a state in which an amplification operation is stopped. The preamplifier 103 may include an amplifier main unit that amplifies and outputs the detection signal, and another peripheral circuit. In this case, in the state in which the amplification is stopped, only the operation of the amplifier main unit may be stopped while an operation of the peripheral circuit is continued. Power consumption of the preamplifier 103 in a case where the amplification operation is stopped in the preamplifier 103 is lower than power consumption of the preamplifier 103 in a case where the preamplifier 103 is in an operating state.

The bypass unit 104 is a unit for outputting the detection signal output from the acoustic wave detector 101 without passing through the preamplifier 103. The bypass unit 104 includes a selection switch 105 for selecting whether or not an input node of the preamplifier 103 and an output node of the preamplifier 103 are to be short-circuited. In a case where the selection switch 105 is open, the input node and the output node of the preamplifier 103 are not short-circuited. On the other hand, in a case where the selection switch 105 is closed, the input node and the output node of the preamplifier 103 are short-circuited.

Here, the short-circuit means a state in which two points of an electric circuit are electrically connected to each other with a relatively low impedance. Short-circuiting the input node and the output node of the preamplifier means that the nodes are connected to each other with low impedance, and includes not only connecting the both nodes by a wire but also connecting the both nodes via any element with low impedance. The preamplifier 103 and the bypass unit 104 may be configured as one IC package. An example of such an IC includes NJG 1139UA2 manufactured by JRC Corporation.

The reception circuit 21 of the ultrasonic unit 12 (see FIG. 1) receives the detection signal amplified by the preamplifier 103 or the detection signal output by the bypass unit 104. The controller 28 of the ultrasonic unit 12 also perform control of the preamplifier 103, the selection switch 105, and the transmission and reception changeover switch 106 arranged in the probe 11. In a case where the photoacoustic waves and the reflected ultrasonic waves are detected, the controller 28 sets the connection destination of the acoustic wave detector 101 as the input node of the preamplifier 103 using the transmission and reception changeover switch 106. In a case where transmission of the ultrasonic waves is performed, the controller 28 sets the connection destination of the acoustic wave detector 101 as an output node of the transmission circuit 29 using the transmission and reception changeover switch 106.

In a case where the photoacoustic waves are detected, the controller 28 causes the preamplifier 103 to enter the operating state. Further, the controller 28 selects a path (a first path) in which the detection signal is amplified by the preamplifier 103 and then is input to the reception circuit 21, as a signal path between the acoustic wave detector 101 and the reception circuit 21. Specifically, the controller 28 selects the first path by opening the selection switch 105 so that the input node and the output node of the preamplifier 103 are not short-circuited. In a case where the photoacoustic waves are detected, it is possible to improve a signal to noise ratio (an SN ratio) of the detection signal of the photoacoustic wave that is sampled in the reception circuit 21 and used in subsequent signal processing by amplifying the detection signal of a weak photoacoustic wave using the preamplifier 103.

In a case where the reflected ultrasonic waves are detected, the controller 28 stops the amplification operation of the preamplifier 103, and selects a path (a second path) in which the detection signal is input to the reception circuit via the bypass unit 104 (the selection switch 105) without passing through the preamplifier 103, as the signal path between the acoustic wave detector 101 and the reception circuit 21. Specifically, the controller 28 selects the second path by closing the selection switch 105 and short-circuiting the input node and the output node of the preamplifier 103. Generally, the reflected ultrasonic waves are stronger than photoacoustic waves, and even in a case where the reflected ultrasonic waves are amplified by the preamplifier 103, a merit of improving an SN ratio is often small. In the case where reflected ultrasonic waves are detected, heat generation is suppressed by selecting the second path which does not pass the preamplifier 103 and stopping the amplification in the preamplifier 103.

The controller 28 may control the operation of the preamplifier 103, for example, by controlling power supply to the preamplifier 103. The controller 28 may cause the preamplifier 103 to enter an operating state by performing the power supply to the preamplifier 103, and stop the amplification operation in the preamplifier 103 by stopping the power supply to the preamplifier 103.

Figure 3:
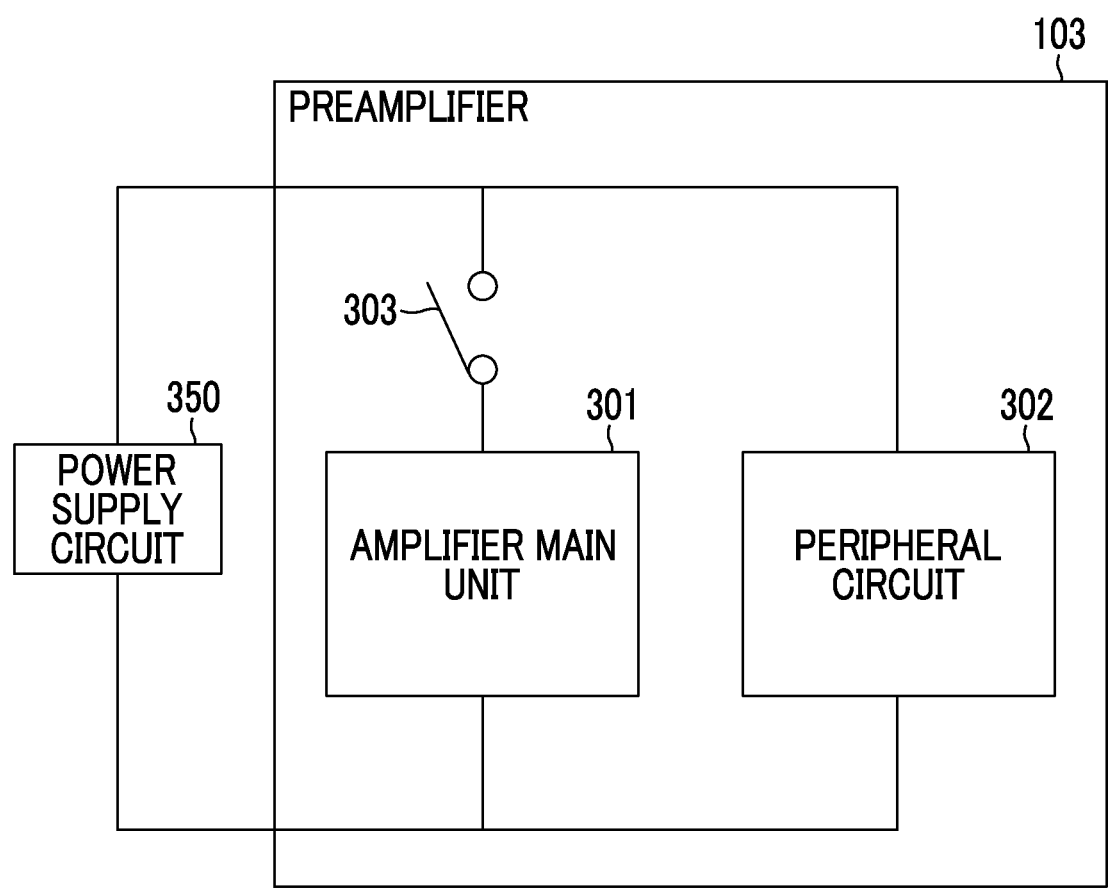
FIG. 3 is a block diagram illustrating a configuration example of a preamplifier.

FIG. 3 illustrates a configuration example of the preamplifier 103. The preamplifier 103 includes, for example, an amplifier main unit 301 that amplifies and outputs the detection signal, and another peripheral circuit 302. The amplifier main unit 301 includes, for example, an operational amplifier configured by, for example, a transistor, or a resistor. The peripheral circuit 302 includes, for example, a communication circuit that performs communication with the controller 28 (see FIGS. 1 and 2). The communication circuit may read, for example, instructions from the controller 28 by discriminating whether a signal level of a specific signal line is high or low. Serial communication such as serial peripheral interface (SPI) or inter-integrated circuit (I2C) may be used for communication with the controller 28.

Power is supplied from the power supply circuit 350 to the amplifier main unit 301 and the peripheral circuit 302. A voltage of the power supplied from the power supply circuit 350 may be different between the amplifier main unit 301 and the peripheral circuit 302. For example, the controller 28 may stop only power supply to the amplifier main unit 301 by opening a power switch 303. In this case, power supply to the amplifier main unit 301 is blocked, and the amplification operation in the preamplifier 103 is stopped. In a case where the power supply to the peripheral circuit 302 is continued, the preamplifier 103 can continue the communication with the controller 28.

In the preamplifier 103, a portion in which power consumption is high is a portion of the amplifier main unit 301 that performs the amplification operation of the detection signal. The peripheral circuit 302 consumes less power than the amplifier main unit 301. Therefore, by stopping the power supply to the amplifier main unit 301 in the preamplifier 103, it is possible to effectively reduce the power consumption of the preamplifier 103. When the power consumption can be reduced, heat generation of the preamplifier 103 can be correspondingly suppressed. It is also possible to stop the amplification operation in the preamplifier 103 by stopping the power supply to the entire preamplifier 103, instead of stopping only the power supply to the amplifier main unit 301.

The controller 28 stopping the amplification operation in the preamplifier 103 by controlling the power supply has been described above, but the present invention is not limited thereto. For example, in a case where the peripheral circuit 302 includes a mode switching unit that switches an operation mode between an operation mode (a first operation mode) in which amplification of the detection signal is performed in the amplifier main unit 301 and an operation mode (a second operation mode) in which the amplification of the detection signal in the amplifier main unit 301 is stopped, the controller 28 may cause the mode switching unit to select the first operation mode in a case where the photoacoustic waves are detected, and cause the mode switching unit to select the second operation mode in a case where the reflected ultrasonic waves are detected. In this case, power consumption can be reduced by stopping the amplification operation, and heat generation can be suppressed.

Figure 4:
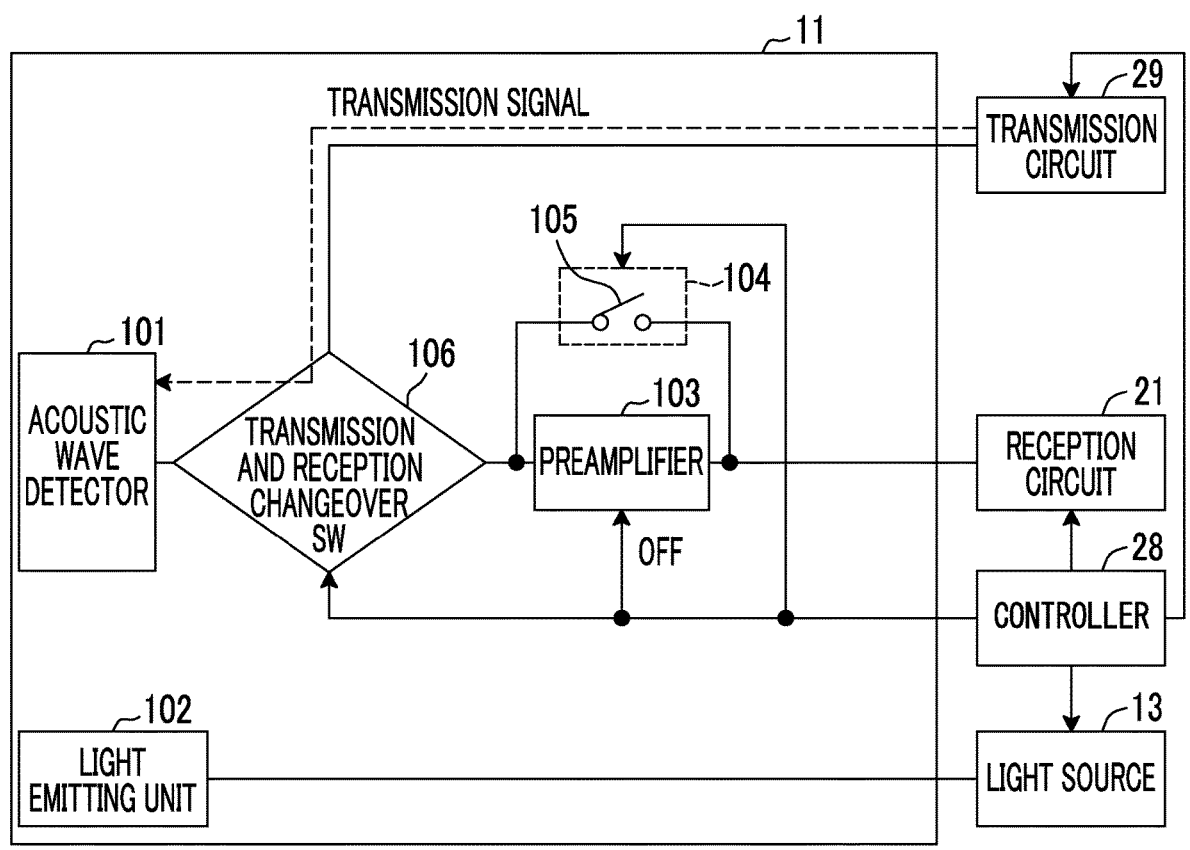
FIG. 4 is a block diagram illustrating a signal path of a transmission signal in a case where ultrasonic waves are transmitted.

FIG. 4 illustrates the signal path of the transmission signal in a case where the ultrasonic waves are transmitted. In a case where the ultrasonic waves are transmitted, the controller 28 connects the transmission circuit 29 to the acoustic wave detector 101 using the transmission and reception changeover switch 106. The transmission signal transmitted by the transmission circuit 29 is input to the acoustic wave detector 101 via the transmission and reception changeover switch 106 as indicated by a broken line in FIG. 4. Since the transmission and reception changeover switch 106 selects the transmission circuit 29 as a connection destination of the acoustic wave detector 101, the transmission signal transmitted by the transmission circuit 29 is not input to the preamplifier 103. In the case where the ultrasonic waves are transmitted, the controller 28 stops the amplification operation in the preamplifier 103, for example, by stopping (OFF) the power supply to the preamplifier 103. Therefore, heat generation in the preamplifier 103 is suppressed in a period in which the ultrasonic waves are transmitted.

Figure 5:
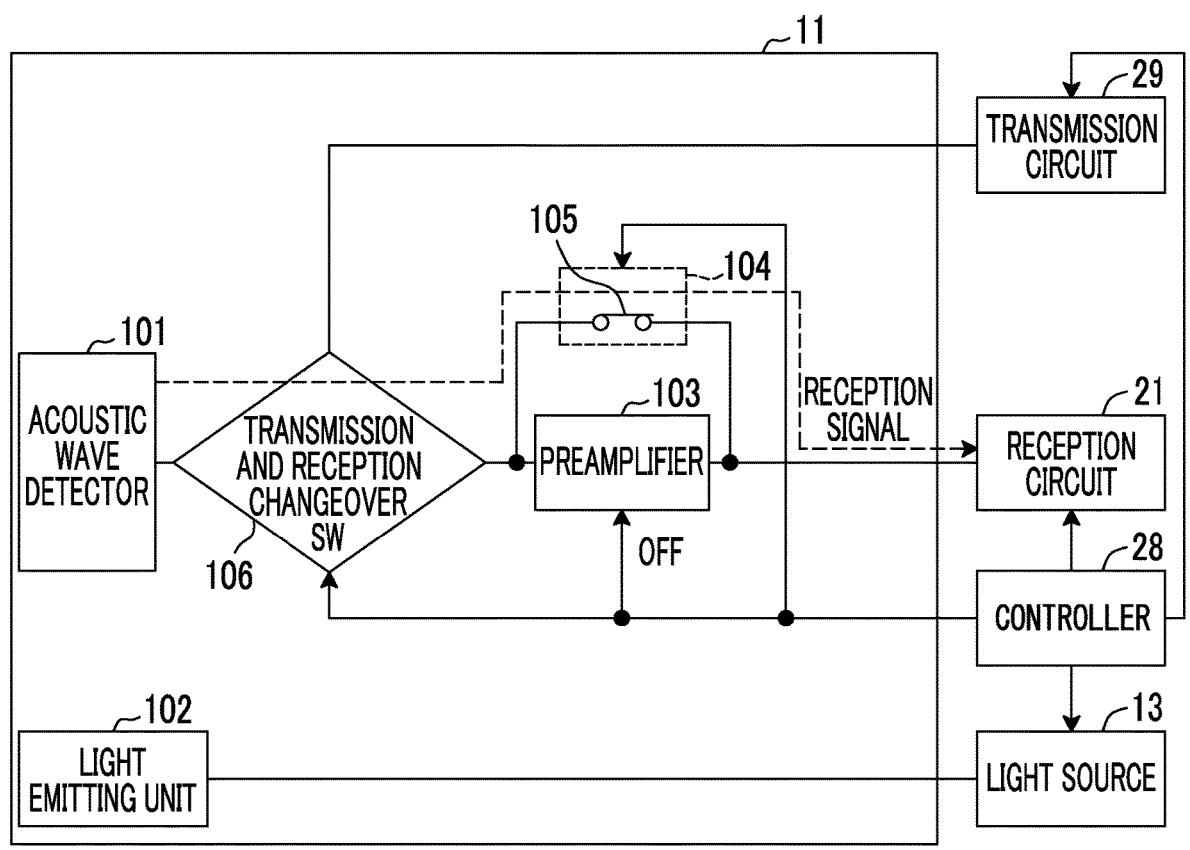
FIG. 5 is a block diagram illustrating a signal path of a detection signal in a case where reflected ultrasonic waves are detected.

FIG. 5 illustrates a signal path of the detection signal in a case where the reflected ultrasonic waves are detected. In a case where the reflected ultrasonic waves are detected, the controller 28 short-circuits the acoustic wave detector 101 and the preamplifier 103 using the transmission and reception changeover switch 106. Further, the controller 28 short-circuits the input node and the output node of the preamplifier 103 using the selection switch 105. As indicated by a broken line in FIG. 5, the detection signal (reception signal) of the reflected ultrasonic waves output from the acoustic wave detector 101 is input to the reception circuit 21 via a path (second path) passing through the bypass unit 104 (the selection switch 105) from the transmission and reception changeover switch 106. In a case where the reflected ultrasonic waves are detected, the controller 28 stops the amplification operation in the preamplifier 103, for example, by stopping (OFF) the power supply to the preamplifier 103. Therefore, heat generation in the preamplifier 103 is suppressed in a period in which the reflected ultrasonic waves are received.

Figure 6:
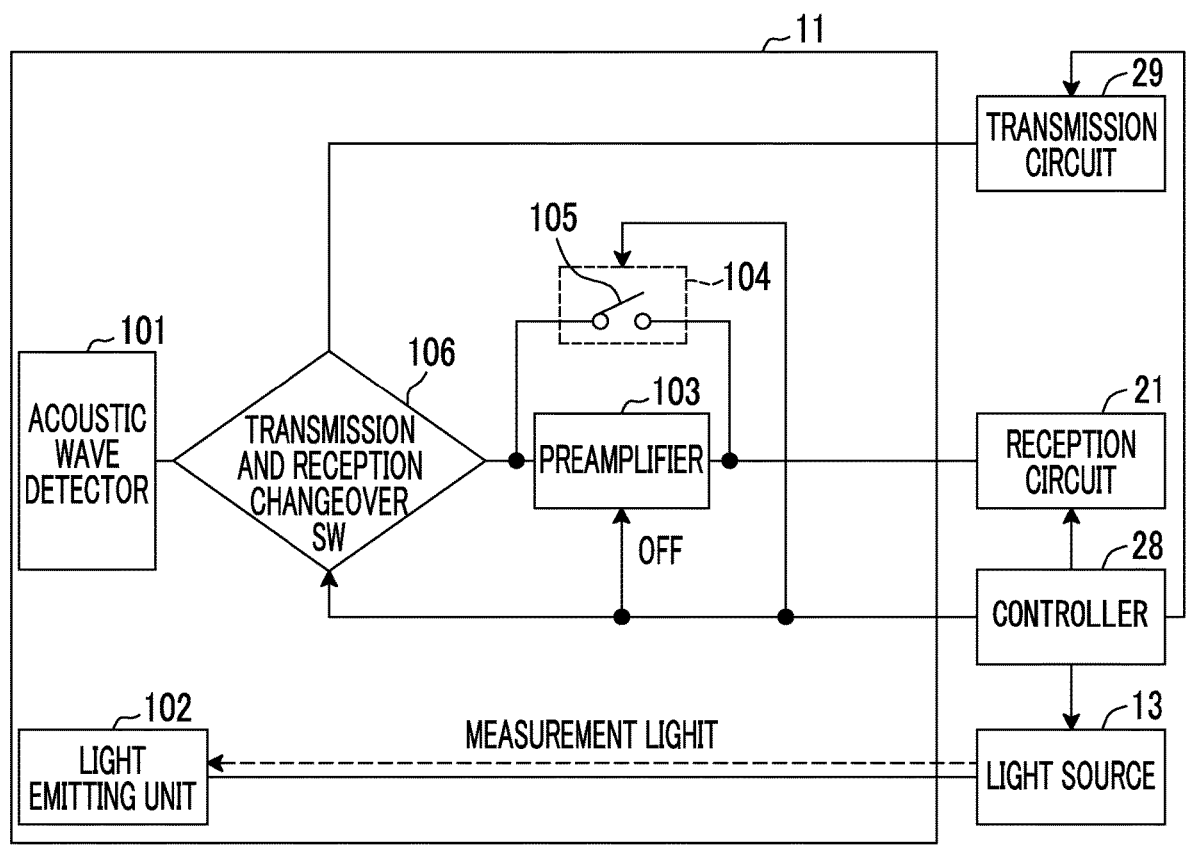
FIG. 6 is a block diagram illustrating a path of measurement light in a case where irradiation of measurement light is performed.

FIG. 6 illustrates a path of the measurement light in a case where irradiation of the measurement light is performed. In a case where irradiation of the measurement light is performed, the controller 28 outputs a light trigger signal to the light source 13 and causes the measurement light to be output from the light source 13. The measurement light output from the light source 13 is incident on the light emitting unit 102 via a bundle fiber or the like as indicated by a broken line in FIG. 6, and is radiated onto the subject from the light emitting unit 102. In a case where the irradiation of the measurement light is performed, no transmission and reception of an electrical signal occurs in the probe 11. Therefore, from the viewpoint of suppression of heat generation, it is preferable to stop the amplification operation in the preamplifier 103, for example, by stopping (OFF) the power supply to the preamplifier 103.

Figure 7:
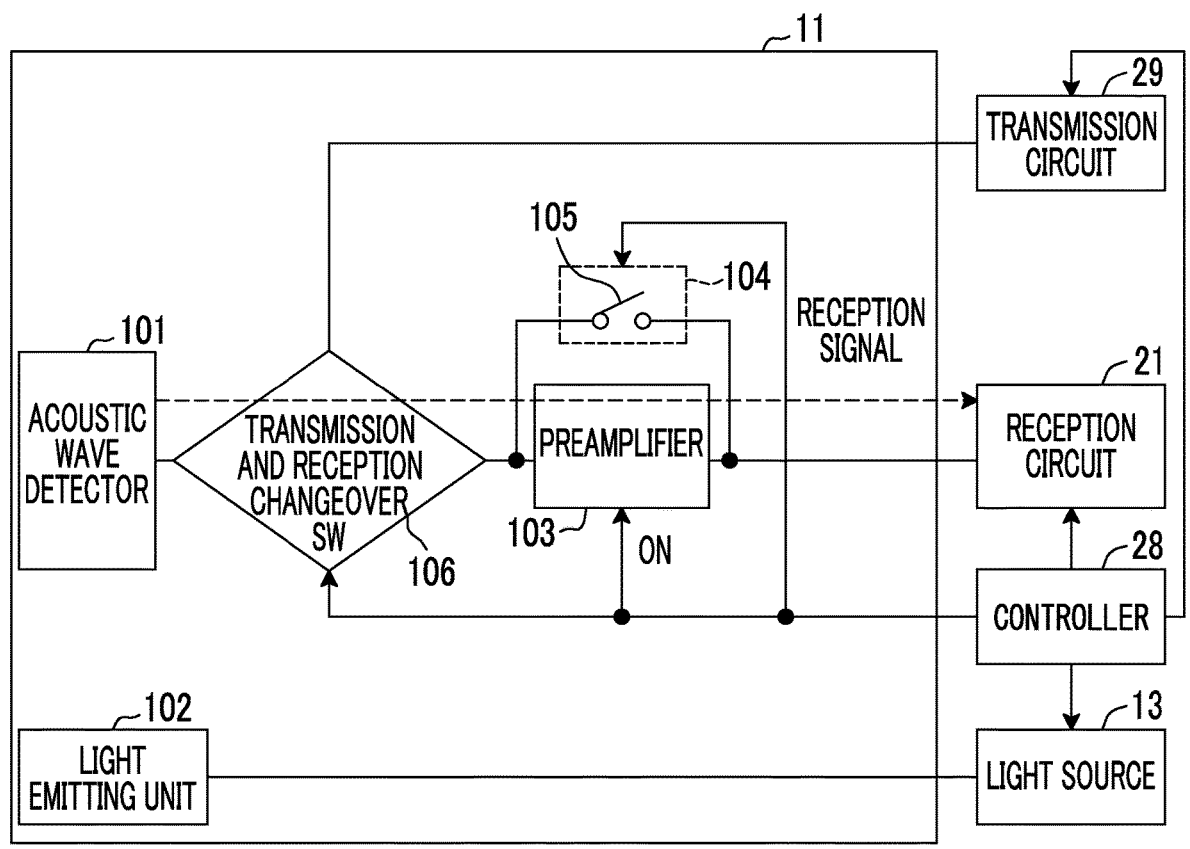
FIG. 7 is a block diagram illustrating a signal path of a detection signal in a case where photoacoustic waves are detected.

FIG. 7 illustrates a signal path of the detection signal in a case where the photoacoustic waves are detected. In a case where the photoacoustic waves are detected, the controller 28 connects the acoustic wave detector 101 to the preamplifier 103 using the transmission and reception changeover switch 106. Further, the controller 28 opens the selection switch 105 and does not short-circuit the input node and the output node of the preamplifier 103. As indicated by a broken line in FIG. 7, the detection signal (reception signal) of the photoacoustic waves output from the acoustic wave detector 101 is input to the reception circuit 21 via the path (the first path) passing the preamplifier 103 from the transmission and reception changeover switch 106. In the case where the photoacoustic waves are detected, the controller 28 causes the preamplifier 103 to enter an operating state, for example, by performing (ON) the power supply to the preamplifier 103.

In the case where the irradiation of the measurement light is performed (see FIG. 6), it is preferable that the controller 28 connects the acoustic wave detector 101 to the preamplifier 103 using the transmission and reception changeover switch 106 in preparation for detection of photoacoustic waves subsequent to the irradiation of the measurement light. Further, it is preferable that the selection switch 105 is opened so that the input node and the output node of the preamplifier 103 are not short-circuited. Further, in a standby state in which any of transmission of ultrasonic waves, detection of the reflected ultrasonic waves, irradiation of the measurement light, and detection of the photoacoustic waves is not performed, it is preferable that the amplification operation in the preamplifier 103 is stopped from the viewpoint of suppression of heat generation.

Figure 8:
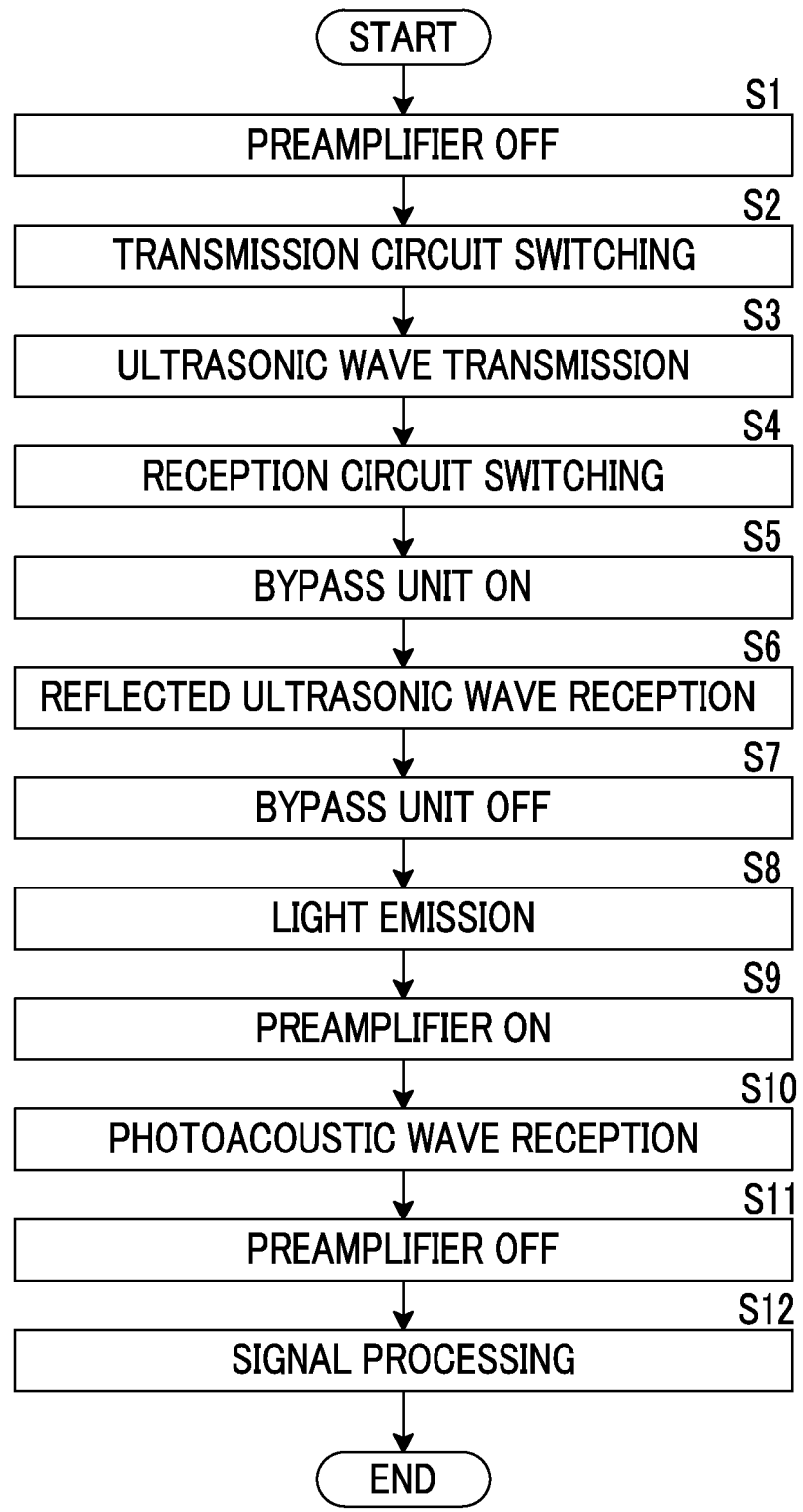
FIG. 8 is a flowchart illustrating an operation procedure of a photoacoustic measurement device.

Next, an operation procedure will be described. FIG. 8 illustrates an operation procedure of the photoacoustic measurement device 10. In a standby state, the controller 28 stops the amplification operation in the preamplifier 103 (preamplifier OFF) (step S1). In a case where ultrasonic waves are transmitted, the controller 28 connects the acoustic wave detector 101 to the transmission circuit 29 using the transmission and reception changeover switch 106 (step S2). The transmission circuit 29 outputs a transmission signal. The acoustic wave detector 101 receives the transmission signal via the transmission and reception changeover switch 106, and performs transmission of the ultrasonic waves to the subject (step S3).

In a case where the transmission of the ultrasonic waves ends, the controller 28 connects the acoustic wave detector 101 to the preamplifier 103 using the transmission and reception changeover switch 106 (step S4). Further, the controller 28 short-circuits the input node and the output node of the preamplifier 103 by closing the selection switch 105 so that the detection signal passes through the bypass unit 104 (bypass unit ON) (step S5). The acoustic wave detector 101 detects reflected ultrasonic waves with respect to the ultrasonic waves transmitted in step S3. The reception circuit 21 receives the detection signal of the reflected ultrasonic waves detected by the acoustic wave detector 101 via the second path (see FIG. 5) passing through the bypass unit 104 (step S6).

In a case where the reception of the reflected ultrasonic waves ends, the controller 28 opens the selection switch 105 so that the detection signal passes through the preamplifier 103 without passing through the bypass unit 104 (bypass unit OFF) (step S7). Step S7 may be performed between the end of the reception of the reflected ultrasonic waves and start of the detection of the photoacoustic waves.

The controller 28 outputs the light trigger signal to the light source 13 and causes the light source 13 to output the measurement light (step S8). The measurement light output from the light source 13 is radiated onto the subject from the light emitting unit 102. The controller 28 causes the preamplifier 103 to enter an operating state (preamplifier ON) (step S9). The acoustic wave detector 101 detects the photoacoustic waves generated by the light absorber in the subject absorbing the measurement light output in step S8. The reception circuit 21 receives the detection signal of the photoacoustic waves detected by the acoustic wave detector 101 via the first path (see FIG. 7) passing through the preamplifier 103 (step S10). In a case where the reception of the photoacoustic waves ends, the controller 28 stops the amplification operation in the preamplifier 103 (preamplifier OFF) (step S11).

The ultrasonic unit 12 (see FIG. 1) performs signal processing on the detection signal of the reflected ultrasonic waves and the detection signal of the photoacoustic waves received by the reception circuit 21 (step S12). In the ultrasonic unit 12, for example, in step S12, the photoacoustic image generation means 24 generates a photoacoustic image. Further, the ultrasonic image generation means 25 generates an ultrasonic image. The photoacoustic image and the ultrasonic image generated in this way are, for example, superimposed or displayed side by side on the image display means 14. Signal processing is not limited to the image generation, and may be processing different from the image generation.

Figure 9:
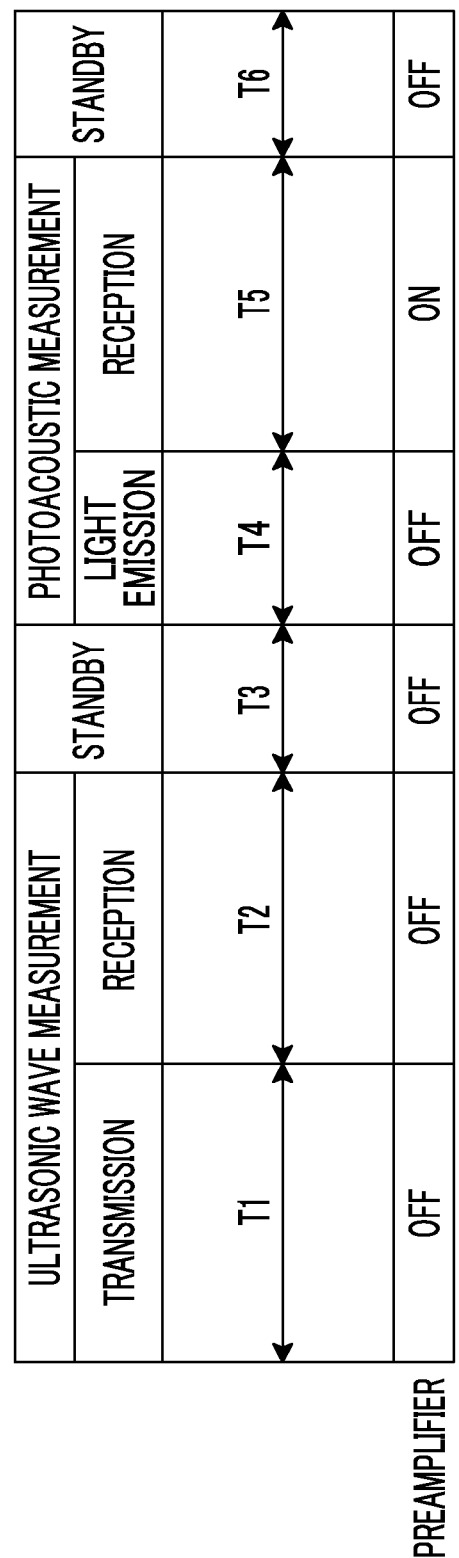
FIG. 9 is a diagram illustrating a series of measurements and an operation status of a preamplifier.

FIG. 9 illustrates a series of measurements, and an operation status of the preamplifier 103. Ultrasonic measurement includes transmission of the ultrasonic waves and reception of the reflected ultrasonic waves, and photoacoustic measurement includes emission of the measurement light and detection (reception) of the photoacoustic waves. In FIG. 9, the photoacoustic measurement is performed after the ultrasonic measurement is performed, but an order of these is not particularly limited. It is also possible to perform one photoacoustic measurement for a plurality of ultrasonic measurements.

In the ultrasonic measurement, a period in which the ultrasonic waves are transmitted is T1, and a period in which the reflected ultrasonic waves are received is T2. In the photoacoustic measurement, a period in which the measurement light is emitted is T4, and a period in which the photoacoustic waves are detected is T5. A standby period is provided between the ultrasonic measurement and the photoacoustic measurement, and after the photoacoustic measurement. The respective standby periods are T3 and T6. In the periods T1 to T4 and T6, the controller 28 stops (OFF) the amplification operation in the preamplifier 103. The controller 28 causes the preamplifier 103 to enter the operating state (ON) only in the period T5 in which the detection of the photoacoustic waves is performed among the periods T1 to T6.

As a comparative example, operating the preamplifier 103 only in a period in which acoustic waves are detected by the acoustic wave detector 101 as in JP2014-198234A is considered. In this case, in the period T2 in which the reflected ultrasonic waves are detected in addition to the periods T5, the preamplifier 103 is controlled so that the preamplifier 103 enters the operating state, and performs the amplification operation. As described above, the reflected ultrasonic waves have higher strength than the photoacoustic waves, and even in a case where the detection signal is amplified by the preamplifier 103, the merit of improving the SN ratio is often small. In this embodiment, since the amplification operation is performed in the preamplifier 103 only in the period in which the photoacoustic waves are detected, an effect of suppressing the heat generation of the preamplifier 103 is higher than in the comparative example, and an increase in the surface temperature of the probe 11 can be further suppressed.

In the embodiment, in a case where the photoacoustic waves are detected by the acoustic wave detector 101, the preamplifier 103 enters the operating state and the first path passing through the preamplifier 103 is selected as a signal path between the acoustic wave detector 101 and the reception circuit 21. Further, in a case where the reflected ultrasonic waves are detected by the acoustic wave detector 101, the amplification operation in the preamplifier 103 is stopped, and the second path passing through the bypass unit 104 is selected as the signal path between the acoustic wave detector 101 and the reception circuit 21. In the embodiment, in a case where the photoacoustic waves are detected, the detection signal of the photoacoustic waves is amplified by the preamplifier 103, and in the case where the reflected ultrasonic waves are detected, the detection signal of the reflected ultrasonic waves is not amplified by the preamplifier 103. Generally, the preamplifier 103 generates heat in a case where the preamplifier 103 amplifies a signal. In the embodiment, since the detection signal is not amplified by the preamplifier 103 in a case where the reflected ultrasonic waves are detected, heat generation in the preamplifier 103 can be correspondingly suppressed.

In the embodiment, in a case where the reflected ultrasonic waves are detected, the selection switch 105 short-circuits the input node and the output node of the preamplifier 103, such that second path in which the detection signal passes through the bypass unit 104 is selected as a signal path to the reception circuit 21. The bypass unit 104 is provided, and even in a case where the acoustic waves are detected in the acoustic wave detector 101, the amplification operation in the preamplifier 103 can be stopped by passing through the bypass unit 104 without passing through the preamplifier 103 in a case where the detected acoustic waves are the reflected ultrasonic waves. By adopting such a configuration, heat generation in the probe 11 including the preamplifier 103 can be further suppressed.

Here, although the probe 11 is a probe for photoacoustic measurement, the probe 11 is not always used for measurement including photoacoustic measurement, and only the ultrasonic measurement may be performed using the probe 11. The embodiment is effective even in imaging in which signal intensity of the detection signal of the reflected ultrasonic waves in an ultrasonic B mode or the like is sufficiently high and improvement of an SN ratio in the preamplifier 103 cannot be greatly expected, by using the probe 11 for photoacoustic measurement. Since the amount of heat generated by the probe 11 can be afforded by the amount of heat generation (the amount of reduction in heat generation) that can be suppressed by stopping the amplification operation in the preamplifier 103 with respect to a maximum allowable amount of heat generation, it is possible to increase a transmission voltage at the time of transmission of ultrasonic waves and increase the amount of heat generation of the acoustic wave detector 101 at the time of transmission of ultrasonic waves by the amount of heat reduction. An ultrasonic image with a higher SN ratio can be obtained by increasing the transmission voltage.

Further, this embodiment is also effective in a case where imaging in which a pulse repetition frequency (PRF) is high in a Doppler mode or the like is performed, by using the probe 11 for photoacoustic measurement. Imaging with a high PRF becomes possible by distributing the amount of heat generation (the amount of reduction in heat generation) that can be suppressed by stopping the amplification operation in the preamplifier 103, to an increase in heat generation of the acoustic wave detector 101 at the time of transmission of the ultrasonic waves. Since the probe for photoacoustic measurement is also used not only for imaging of the photoacoustic image or an image in which the photoacoustic image and the ultrasonic image are superimposed but also for imaging of other ultrasonic images, the embodiment is very effective.

Figure 10:
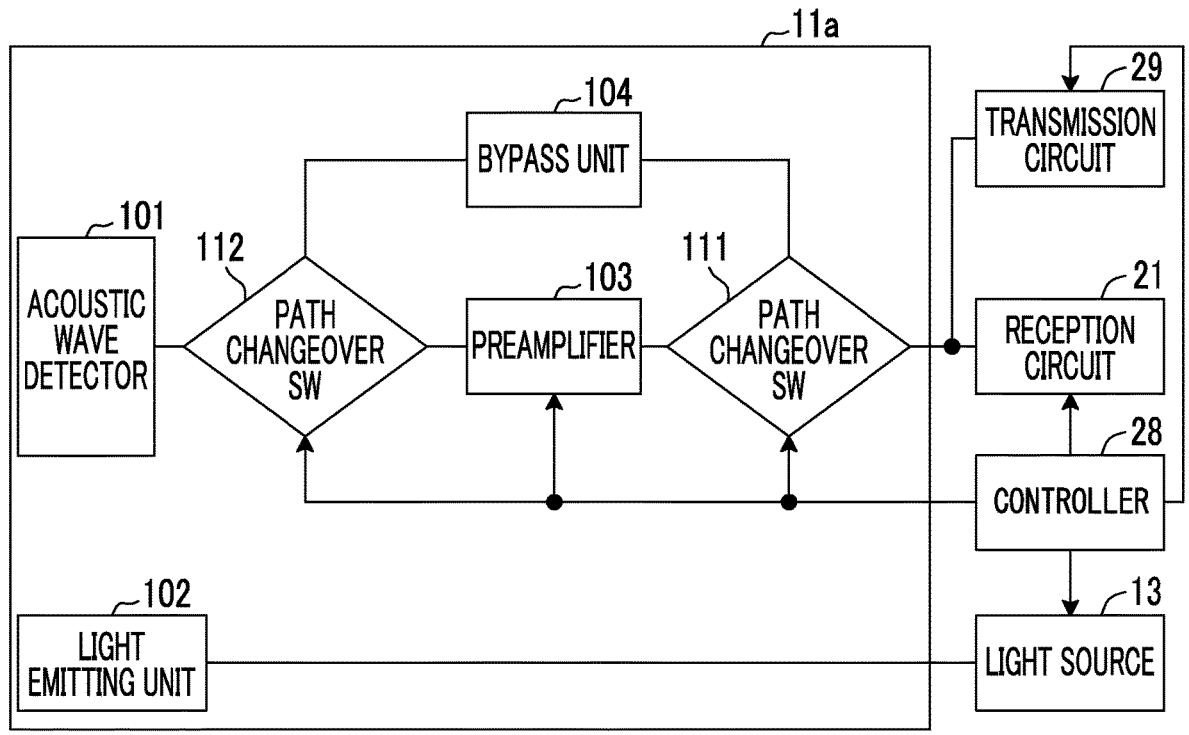
FIG. 10 is a block diagram illustrating a configuration of a probe of a photoacoustic measurement device according to a second embodiment of the present invention.

Next, a second embodiment of the present invention will be described. FIG. 10 illustrates a configuration of a probe of a photoacoustic measurement device according to a second embodiment of the present invention. An overall configuration of the photoacoustic measurement device of this embodiment may be the same as that of the photoacoustic measurement device 10 according to the first embodiment illustrated in FIG. 1. A probe 11a used in the second embodiment includes an acoustic wave detector 101, a light emitting unit 102, a preamplifier 103, a bypass unit 104, a first path changeover switch 111, and a second path changeover switch 112. The acoustic wave detector 101, the light emitting unit 102, and the preamplifier 103 may be the same as those of the probe 11 used in the first embodiment illustrated in FIG. 2.

In the first embodiment, the reception circuit 21 and the transmission circuit 29 are connected to the probe 11 by individual wires as illustrated in FIG. 2, whereas in the second embodiment, the reception circuit 21 and the transmission circuit 29 are connected to the probe 11a via a common wire. In the second embodiment, since the reception circuit 21 and the transmission circuit 29 perform transmission of the transmission signal and reception of the detection signal via the common wire, the number of wires for connecting the probe 11b and the ultrasonic unit 12 (see FIG. 1) can be reduced. In the second embodiment, for example, a protection circuit or the like for preventing the transmission signal output by the transmission circuit 29 from going around may be provided on the input side of the reception circuit 21.

The first path changeover switch 111 switches a connection destination of the wire common to the reception circuit 21 and the transmission circuit 29 between the bypass unit 104 and the preamplifier 103. The second path changeover switch 112 switches the connection destination of the wire connected to the acoustic wave detector 101 between the preamplifier 103 and the bypass unit 104. The bypass unit 104 connects the first path changeover switch 111 to the second path changeover switch 112. The bypass unit 104 is, for example, a wire that connects the first path changeover switch 111 to the second path changeover switch 112.

The controller 28 controls the preamplifier 103, the first path changeover switch Ill, and the second path changeover switch 112. The control of the preamplifier 103 may be similar to that in the first embodiment. That is, in a case where ultrasonic waves are transmitted, a case where the reflected ultrasonic waves are detected, and a case where measurement light is radiated, the controller 28 stops the amplification operation in the preamplifier 103, and in a case where the photoacoustic waves are detected, the controller 28 causes the preamplifier 103 to enter an operating state.

In a case where the photoacoustic waves are detected, the controller 28 connects the wire common to the reception circuit 21 and the transmission circuit 29 to the preamplifier 103 using the first path changeover switch 111. Further, in a case where the photoacoustic waves are detected, the controller 28 connects the wire connected to the acoustic wave detector 101 to the preamplifier 103 using the second path changeover switch 112. Thus, the first path passing through the preamplifier 103 is selected as the signal path between the acoustic wave detector 101 and the reception circuit 21.

In the case where the ultrasonic waves are transmitted and the case where the reflected ultrasonic waves are detected, the controller 28 connects the wire common to the reception circuit 21 and the transmission circuit 29 to the bypass unit 104 using the first path changeover switch 111. In the case where the ultrasonic waves are transmitted and the case where the reflected ultrasonic waves are detected, the controller 28 connects the wire connected to the acoustic wave detector 101 to the bypass unit 104 using the second path changeover switch 112. By doing so, in a case where the ultrasonic waves are transmitted, the transmission signal transmitted from the transmission circuit 29 is input to the acoustic wave detector 101 through the bypass unit 104. In a case where the reflected ultrasonic waves are detected, the second path passing through the bypass unit 104 is selected as the signal path between the acoustic wave detector 101 and the reception circuit 21.

Figure 11:
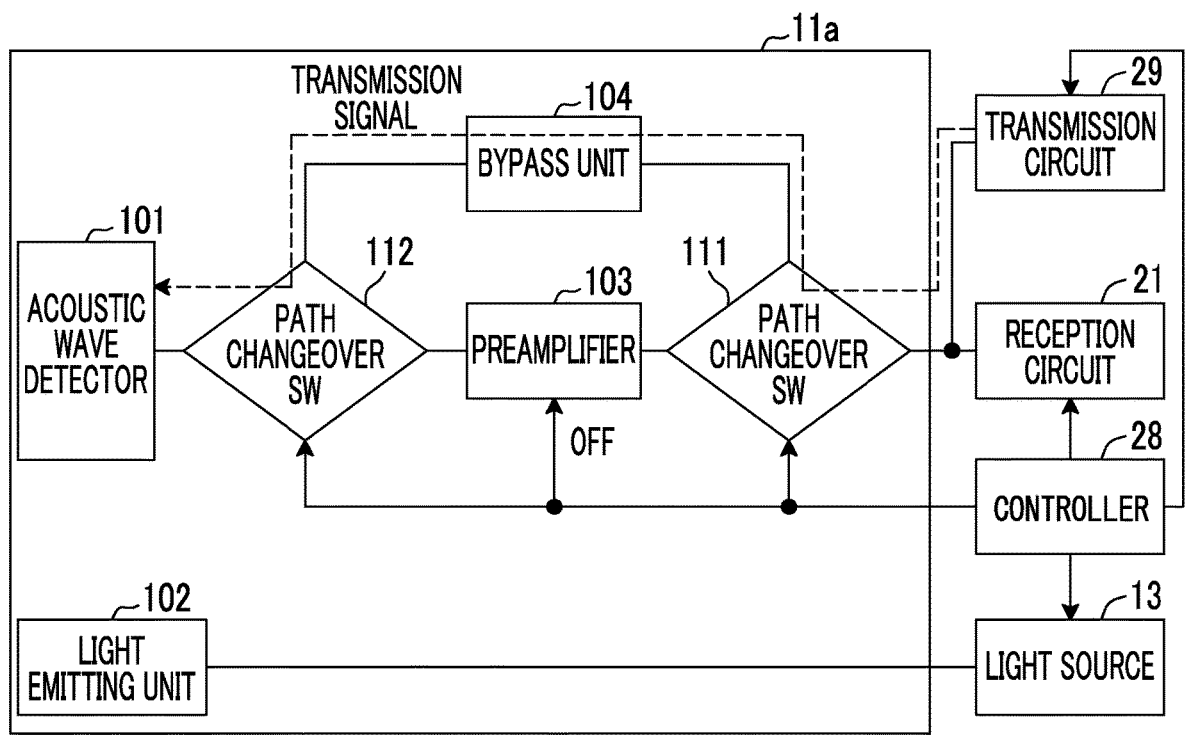
FIG. 11 is a block diagram illustrating a signal path of a transmission signal in a case where ultrasonic waves are transmitted.

FIG. 11 illustrates a signal path of the transmission signal in a case where the ultrasonic waves are transmitted. In a case where the ultrasonic waves are transmitted, the controller 28 connects the wire common to the reception circuit 21 and the transmission circuit 29 to the bypass unit 104 using the first path changeover switch 111, and connects the wire connected to the acoustic wave detector 101 to the bypass unit 104 using the second path changeover switch 112. As indicated by a broken line in FIG. 11, the transmission signal transmitted by the transmission circuit 29 is input to the acoustic wave detector 101 via the first path changeover switch 111, the bypass unit 104, and the second path changeover switch 112. Since the first path changeover switch 111 is used to cause the connection destination of the wire common to the reception circuit 21 and the transmission circuit 29 to be the bypass unit 104, and the second path changeover switch 112 is used to cause the connection destination of the wire connected to the acoustic wave detector 101 to be the bypass unit 104, the transmission signal transmitted by the transmission circuit 29 is not input to the preamplifier 103. In the case where the ultrasonic waves are transmitted, the controller 28 stops the amplification operation in the preamplifier 103, for example, by stopping (OFF) the power supply to the preamplifier 103. Therefore, heat generation in the preamplifier 103 is suppressed in a period in which ultrasonic waves are being transmitted.

Figure 12:
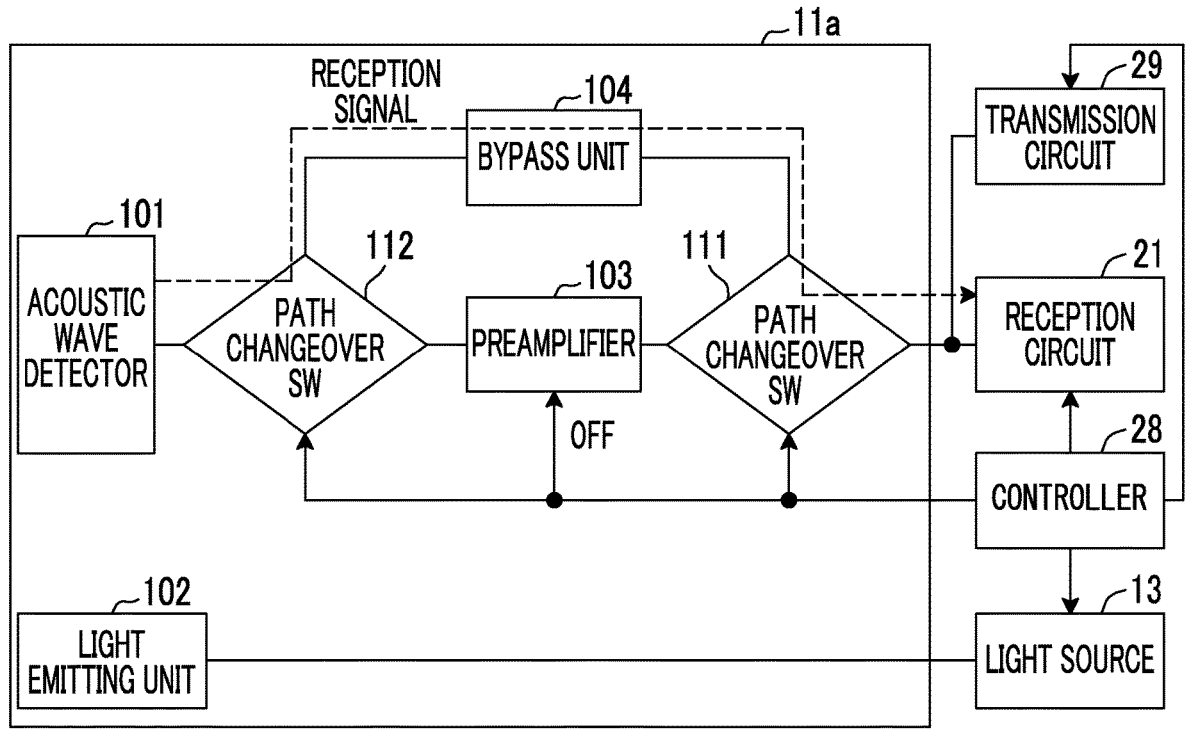
FIG. 12 is a block diagram illustrating a signal path of a detection signal in a case where reflected ultrasonic waves are detected.

FIG. 12 illustrates a signal path of the detection signal in the case where reflected ultrasonic waves are detected. In the case of reflected ultrasonic waves are detected, the controller 28 connects the wire common to the reception circuit 21 and the transmission circuit 29 to the bypass unit 104 using the first path changeover switch 111 and connects the wire connected to the acoustic wave detector 101 to the bypass unit 104 using the second path changeover switch 112 as in the case of FIG. 11. The detection signal (reception signal) of the reflected ultrasonic waves output by the acoustic wave detector 101 is input to the reception circuit 21 via a path (the second path) passing through the second path changeover switch 112, the bypass unit 104, and the first path changeover switch 111, as indicated by a broken line in FIG. 12. In the case where the reflected ultrasonic waves are detected, the controller 28 stops the amplification operation in the preamplifier 103, for example, by stopping (OFF) the power supply to the preamplifier 103. Therefore, heat generation in the preamplifier 103 is suppressed in the period in which the reflected ultrasonic waves are received.

Figure 13:
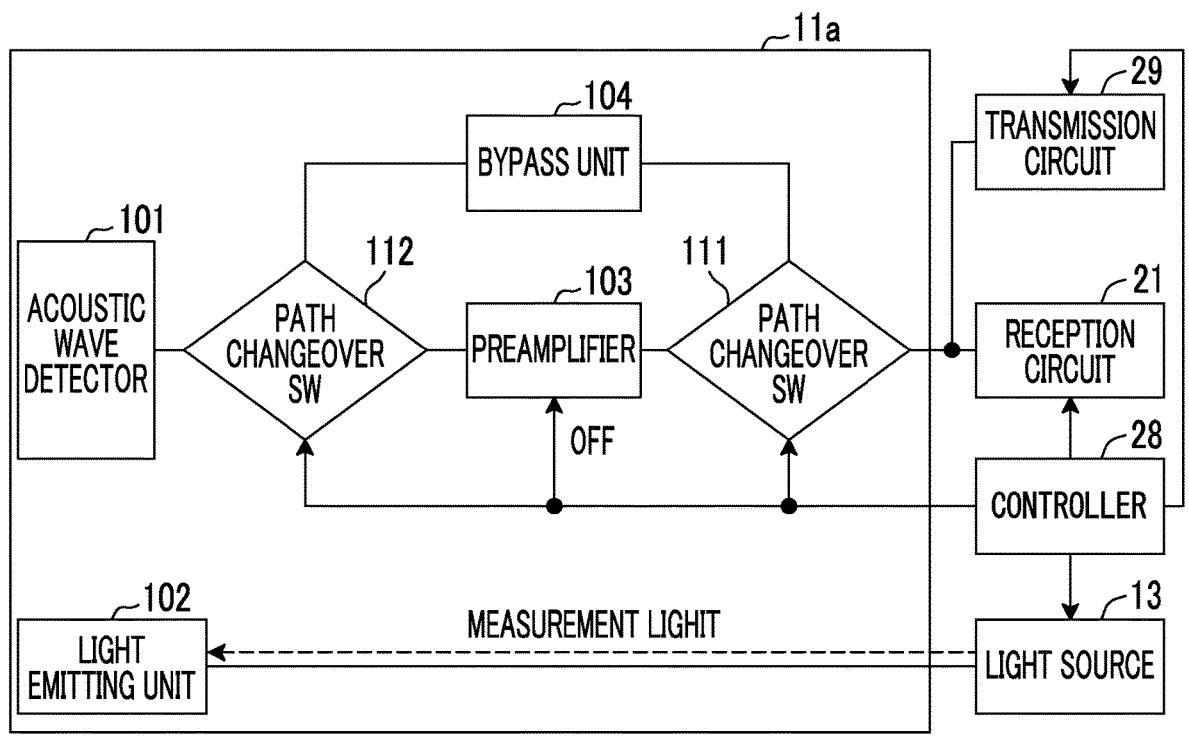
FIG. 13 is a block diagram illustrating a path of measurement light in a case where irradiation of measurement light is performed.

FIG. 13 illustrates a path of the measurement light in a case where irradiation of the measurement light is performed. In a case where irradiation of the measurement light is performed, the controller 28 outputs a light trigger signal to the light source 13 and causes the measurement light to be output from the light source 13. The measurement light output from the light source 13 is incident on the light emitting unit 102 via a bundle fiber or the like, and is radiated onto the subject from the light emitting unit 102, as indicated by a broken line in FIG. 13. In the case where the irradiation of the measurement light is performed, no transmission and reception of an electrical signal occurs in the probe 111, and therefore, it is preferable from the viewpoint of suppression of heat generation that the amplification operation in the preamplifier 103 is stopped, for example, by stopping (OFF) the power supply to the preamplifier 103.

Figure 14:
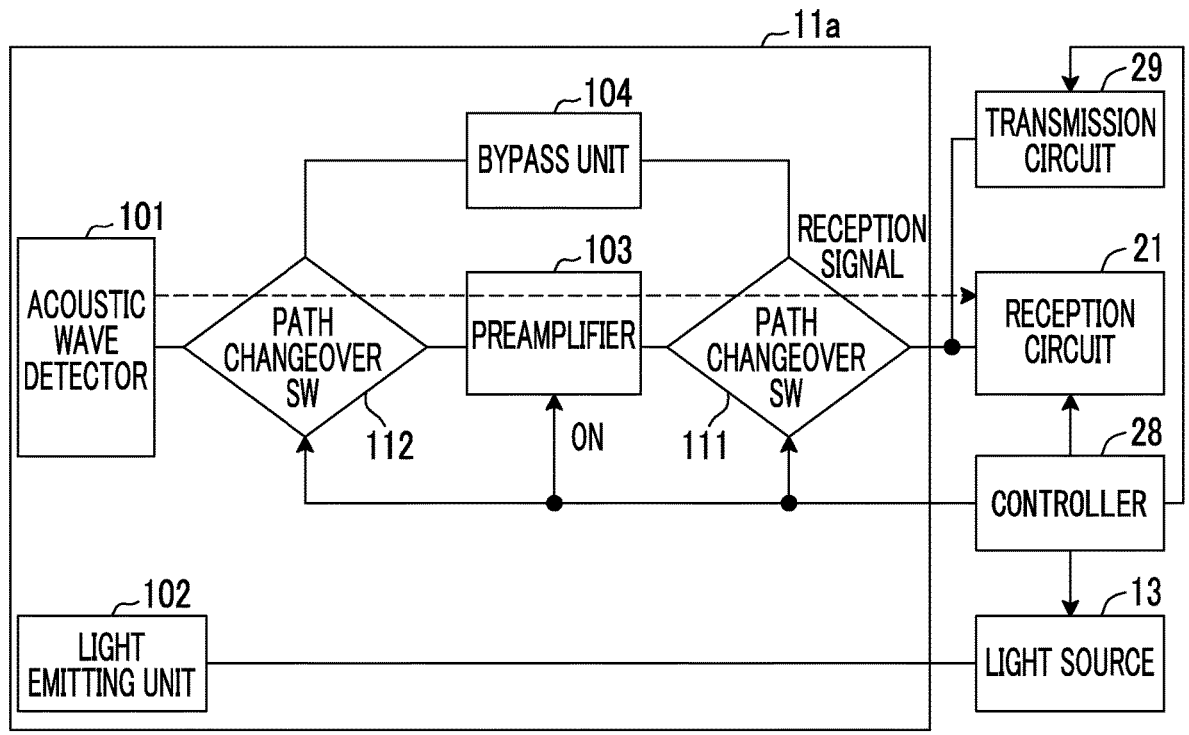
FIG. 14 is a block diagram illustrating a signal path of a detection signal in a case where photoacoustic waves are detected.

FIG. 14 illustrates a signal path of the detection signal in a case where the photoacoustic waves are detected. In a case where the photoacoustic waves are detected, the controller 28 connects the wire common to the reception circuit 21 and the transmission circuit 29 to the preamplifier 103 using the first path changeover switch 111, and connects the wire connected to the acoustic wave detector 101 to the preamplifier 103 using the second path changeover switch 112. As indicated by a broken line in FIG. 14, the detection signal (reception signal) of the photoacoustic waves output from the acoustic wave detector 101 is input to the reception circuit 21 via a path (the first path) passing through the second path changeover switch 112, the preamplifier 103, and the first path changeover switch 111. In the case where photoacoustic waves are detected, the controller 28 causes the preamplifier 103 to enter an operating state, for example, by performing (ON) the power supply to the preamplifier 103.

In a case where the irradiation of the measurement light is performed (see FIG. 13), it is preferable that the controller 28 connects the wire common to the reception circuit 21 and the transmission circuit 29 to the preamplifier 103 using the first path changeover switch 111, and connects the wire connected to the acoustic wave detector 101 to the preamplifier 103 using the second path changeover switch 112 in preparation for detection of the photoacoustic waves subsequent to the irradiation of the measurement light. Further, in a standby state in which any of transmission of ultrasonic waves, detection of the reflected ultrasonic waves, irradiation of the measurement light, and detection of the photoacoustic waves is not performed, it is preferable that the amplification operation in the preamplifier 103 is stopped from the viewpoint of suppression of heat generation.

In the embodiment, the first path changeover switch 111 and the second path changeover switch 112 are used in place of the transmission and reception changeover switch 106 (see FIG. 2). In the case where photoacoustic waves are detected, the wire common to the reception circuit 21 and the transmission circuit 29 is connected to the preamplifier 103 by the first path changeover switch 111, and the wire connected to the acoustic wave detector 101 is connected to the preamplifier 103 by the second path changeover switch 112, such that the detection signal of the photoacoustic waves can be received via the path passing through the preamplifier 103. In the case where the ultrasonic waves are transmitted and the case where the reflected ultrasonic waves are detected, the path common to the reception circuit 21 and the transmission circuit 29 is connected to the bypass unit 104 by the first path changeover switch 111, and the wire connected to the acoustic wave detector 101 is connected to the bypass unit 104 by the second path changeover switch 112, such that the transmission signal of the ultrasonic waves and the detection signal of the reflected ultrasonic waves can be transmitted and received via the path passing through the bypass unit 104. In the configuration of the embodiment, heat generation in the probe 11 including the preamplifier 103 can be further suppressed as in the first embodiment. Other effects are similar to those of the first embodiment.

Figure 15:
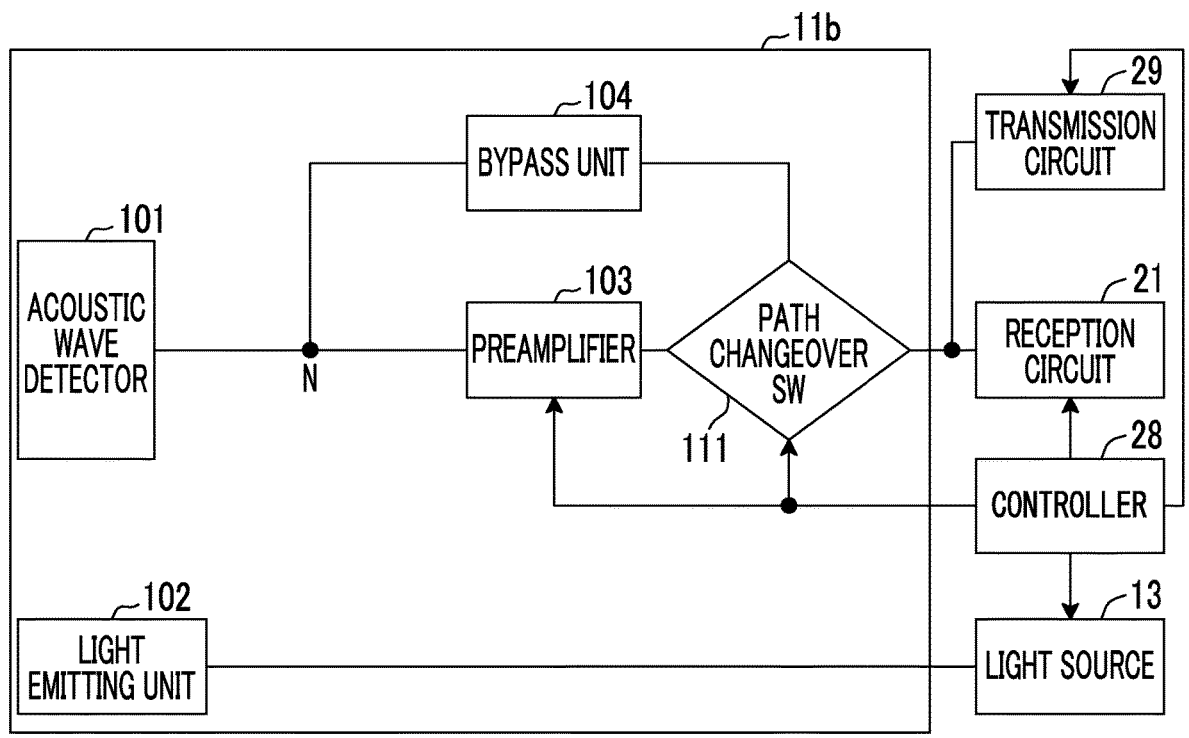
FIG. 15 is a block diagram illustrating a probe according to a modification example of the second embodiment.

In the second embodiment, the path changeover switches are arranged on both of the input side and the output side of the preamplifier 103, but the path changeover switch may be arranged at least on the output side of the preamplifier 103, and the path changeover switch (the second path changeover switch 112) on the input side of the preamplifier 103 may be omitted. FIG. 15 illustrates a probe according to a modification example of the second embodiment. The probe of the modification example has a configuration in which the second path changeover switch 112 (see FIG. 10) is replaced with a signal branching node N that branches the detection signal of the acoustic wave detector 101.

In the probe 11b of the modification example, the signal branching node N is provided between the acoustic wave detector 101 and the input node of the preamplifier 103. The bypass unit 104 is arranged between the signal branching node N and a first path changeover switch (hereinafter referred to simply as a path changeover switch) 111. In a case where the path changeover switch 111 connects the wire common to the reception circuit 21 and the transmission circuit 29 to the bypass unit 104, the common wire is connected to the acoustic wave detector 101 via the bypass unit 104. In a case where the path changeover switch 111 connects the wire common to the reception circuit 21 and the transmission circuit 29 to the preamplifier 103, the common wire is connected to the acoustic wave detector 101 via the preamplifier 103.

In a case where the controller 28 detects the photoacoustic waves, the path changeover switch 11 connects the wire common to the reception circuit 21 and the transmission circuit 29 to the preamplifier 103, as in the second embodiment. In this case, the detection signal (reception signal) of the photoacoustic waves output by the acoustic wave detector 101 is input to the reception circuit 21 via a path (the first path) passing through the signal branching node N, the preamplifier 103, and the path changeover switch 111. The detection signal of the photoacoustic waves output by the acoustic wave detector 101 is also transmitted to the bypass unit 104, but since the path changeover switch 11 connects the wire common to the reception circuit 21 and the transmission circuit 29 to the preamplifier 103, the signal passing through the bypass unit 104 is not received by the reception circuit 21.

The controller 28 connects the wire common to the reception circuit 21 and the transmission circuit 29 to the bypass unit 104 using the path changeover switch 111 in the case where the ultrasonic waves are transmitted and the case where reflected ultrasonic waves are detected, as in the second embodiment. In the case where the reflected ultrasonic waves are detected, the detection signal (reception signal) of the reflected ultrasonic waves output by the acoustic wave detector 101 is input to the reception circuit 21 via a path (the second path) passing through the signal branching node N, the bypass unit 104, and the path changeover switch 11. The detection signal of the reflected ultrasonic waves output by the acoustic wave detector 101 is also transmitted to the preamplifier 103, but since the path changeover switch 111 connects the wire common to the reception circuit 21 and the transmission circuit 29 to the bypass unit 104, the signal passing through the preamplifier 103 is not received by the reception circuit 21.

In the case where the ultrasonic waves are transmitted, the transmission signal transmitted by the transmission circuit 29 is input to the acoustic wave detector 101 via the path changeover switch 111, the bypass unit 104, and the signal branching node N. In the modification illustrated in FIG. 15, in the case where the ultrasonic waves are transmitted, the input node of the preamplifier 103 is always connected to the acoustic wave detector 101, and therefore, the transmission signal is input to the preamplifier 103 at the time of transmission of the ultrasonic waves. In order to prevent a problem caused by the input of the transmission signal to the preamplifier 103, a protection circuit that protects the preamplifier 103 from the transmission signal may be provided at a stage before the input node of the preamplifier 103.

Although only one bypass unit 104 is depicted in FIGS. 9 and 15, a plurality of bypass units 104 may be provided. For example, a bypass unit through which a transmission signal passes and a bypass unit through which a detection signal of reflected ultrasonic waves passes may be provided, and switching between these bypass units may occur in a case where ultrasonic waves are transmitted and a case where reflected ultrasonic waves are detected. Further, the bypass unit 104 is not limited to a mere wire, and may include some element having low impedance with respect to a signal passing through the bypass unit. Particularly, in the case where the bypass unit through which the transmission signal passes and the bypass unit through which the detection signal of the reflected ultrasonic wave passes are provided, the bypass unit through which the transmission signal passes may include an element such as a diode, for example.

In the first embodiment, the transmission and reception changeover switch 106 causes the connection destination of the acoustic wave detector 101 to be the output node of the transmission circuit 29 in a case where the transmission of the ultrasonic waves is performed, and whereas, the transmission and reception changeover switch 106 causes the connection destination of the acoustic wave detector 101 to be the input node of the preamplifier 103 in a case where the photoacoustic waves and the reflected ultrasonic waves are detected. The transmission and reception changeover switch 106 causes the connection destination of the acoustic wave detector 101 to be the preamplifier 103 in a case where the photoacoustic waves are detected, and the connection destination of the acoustic wave detector 101 to be the bypass unit 104 (closed selection switch 105) in a case where the reflected ultrasonic waves are detected in combination with the selection switch 105, but the present invention is not limited thereto. Instead of using the selection switch that short-circuits the input node and the output node of the preamplifier 103, the transmission and reception changeover switch 106 alone is used to cause the connection destination of the acoustic wave detector 101 to be the preamplifier 103 in a case where the photoacoustic waves are detected, cause the connection destination of the acoustic wave detector 101 to be the bypass unit 104 in a case where reflected ultrasonic waves are detected, and cause the connection destination of the acoustic wave detector 101 to be the transmission circuit 29 in a case where transmission of the ultrasonic waves is performed.

Although the present invention has been described on the basis of the preferred embodiments thereof, the photoacoustic measurement device and method of the present invention are not limited only to the above-described embodiments, and various corrections and modifications of the configurations of the above embodiments are included within the scope of the present invention.

In the present invention, the bypass unit may include a selection switch that selects whether or not to short-circuit an input node of the preamplifier and an output node of the preamplifier. In this case, the controller may further control the selection switch to select the first path by not short-circuiting the input node and the output node using the selection switch in a case where the photoacoustic waves are detected, and to select the second path by short-circuiting the input node and the output node using the selection switch in a case where the reflected acoustic waves are detected.

The photoacoustic measurement device of the present invention may further comprise: an acoustic wave transmitter that performs transmission of the acoustic waves to the subject; and a transmission circuit that outputs a transmission signal for causing the acoustic wave transmitter to transmit the acoustic waves from the acoustic wave detector. In this case, the acoustic wave detector may also serve as the acoustic wave transmitter.

The probe may further include a transmission and reception changeover switch that switches a connection destination of the acoustic wave detector between the preamplifier and the transmission circuit. In this case, the controller may further control the transmission and reception changeover switch to cause the connection destination of the acoustic wave detector to be the preamplifier in a case where the photoacoustic waves are detected, the connection destination of the acoustic wave detector to be the bypass unit in a case where the reflected acoustic waves are detected, and the connection destination of the acoustic wave detector to be the transmission circuit in a case where transmission of the acoustic waves is performed.

In the photoacoustic measurement device of the present invention, the probe may further include a first path changeover switch that switches a connection destination of a wire connected to the reception circuit between the bypass unit and the preamplifier, and a second path changeover switch that switches a connection destination of a wire connected to the acoustic wave detector between the preamplifier and the bypass unit. In this case, the controller may further control the first path changeover switch and the second path changeover switch, select the first path by connecting the wire connected to the reception circuit to the preamplifier using the first path changeover switch and connecting a wire connected to the acoustic wave detector to the preamplifier using the second path changeover switch in a case where the photoacoustic waves are detected, and select the second path by connecting the wire connected to the reception circuit to the bypass unit using the first path changeover switch and connecting the wire connected to the acoustic wave detector to the bypass unit using the second path changeover switch in a case where the reflected acoustic waves are detected.

In the above, the photoacoustic measurement device of the present invention may further comprise: an acoustic wave transmitter that performs transmission of the acoustic waves to the subject; and a transmission circuit that outputs a transmission signal for causing the acoustic wave transmitter to transmit the acoustic waves from the acoustic wave transmitter. The acoustic wave detector may also serve as the acoustic wave transmitter, the transmission circuit and the reception circuit may be connected to the first path changeover switch via a common wire, and the first path changeover switch may switch a connection destination of the common wire between the bypass unit and the preamplifier. In this case, in a case where transmission of the acoustic waves is performed, the controller may also connect the common wire to the bypass unit using the first path changeover switch, and connect a wire connected to the acoustic wave detector to the bypass unit using the second path changeover switch.

Alternatively, in the photoacoustic measurement device of the present invention, the probe may further include a first path changeover switch that switches a connection destination of a wire connected to the reception circuit between the bypass unit and the preamplifier, and the bypass unit may be arranged between a signal branching node provided between the acoustic wave detector and an input node of the preamplifier and the first path changeover switch. In this case, the controller may further control the first path changeover switch, select the first path by connecting the wire connected to the reception circuit to the preamplifier using the first path changeover switch in a case where the photoacoustic waves are detected, and select the second path by connecting the wire connected to the reception circuit to the bypass unit using the first path changeover switch in a case where the reflected acoustic waves are detected.

In the above, the photoacoustic measurement device of the present invention may further comprise: an acoustic wave transmitter that performs transmission of the acoustic waves to the subject; and a transmission circuit that outputs a transmission signal for causing the acoustic wave transmitter to transmit the acoustic waves from the acoustic wave transmitter. The acoustic wave detector may also serve as the acoustic wave transmitter, the transmission circuit and the reception circuit may be connected to the first path changeover switch via a common wire, and the first path changeover switch may switch a connection destination of the common wire between the bypass unit and the preamplifier. In this case, in a case where transmission of the acoustic waves is performed, the controller may also connect the common wire to the bypass unit using the first path changeover switch.

In the present invention, it is preferable that the probe further includes a light emitting unit that emits the measurement light toward the subject.

The controller may control an operation of the preamplifier by controlling power supply to the preamplifier. In this case, the controller may cause the preamplifier to enter an operating state by supplying power to the preamplifier, and stop an amplification operation in the preamplifier by stopping the power supply to the preamplifier.

The preamplifier may include an amplifier main unit that amplifies and outputs the detection signal, and the controller may stop the amplification operation in the preamplifier by stopping at least the power supply to the amplifier main unit.

Alternatively, the preamplifier may include an amplifier main unit that amplifies and outputs the detection signal, and a mode switching unit that switches an operation mode between a first operation mode in which amplification of the detection signal is performed in the amplifier main unit and a second operation mode in which at least the amplification of the detection signal is stopped in the amplifier main unit. In this case, the controller may cause the mode switching unit to select the first operation mode in a case where the photoacoustic waves are detected, and cause the mode switching unit to select the second operation mode in the case where the reflected acoustic waves are detected.

The photoacoustic measurement device and method of the present invention enable further suppression of heat generation in a probe including a preamplifier.

What is claimed is:

1. A photoacoustic measurement device comprising:
a probe including an acoustic wave detector that detects photoacoustic waves generated by a light absorber in a subject absorbing measurement light emitted toward the subject and reflected acoustic waves with respect to acoustic waves transmitted toward the subject and outputs a detection signal, a preamplifier that amplifies the detection signal output by the acoustic wave detector, and a selection switch that outputs the detection signal without passing through the preamplifier, wherein the selection switch selects whether or not to short-circuit an input node of the preamplifier and an output node of the preamplifier;
a reception circuit that receives the detection signal amplified by the preamplifier or the detection signal output by the selection switch; and
controller for causing the preamplifier to enter an operating state and selecting a first path along which the detection signal is amplified by the preamplifier and then is input to the reception circuit as a signal path between the acoustic wave detector and the reception circuit in a case where the photoacoustic waves are detected by the acoustic wave detector, and for stopping an amplification operation in the preamplifier and selecting a second path along which the detection signal is input to the reception circuit through the selection switch as the signal path in a case where the reflected acoustic waves are detected by the acoustic wave detector.

2. The photoacoustic measurement device according to claim 1,
the controller further controls the selection switch to select the first path by not short-circuiting the input node and the output node using the selection switch in a case where the photoacoustic waves are detected, and to select the second path by short-circuiting the input node and the output node using the selection switch in a case where the reflected acoustic waves are detected.

3. The photoacoustic measurement device according to claim 1, further comprising:
an acoustic wave transmitter that performs transmission of the acoustic waves to the subject; and
a transmission circuit that outputs a transmission signal for causing the acoustic wave transmitter to transmit the acoustic waves from the acoustic wave detector,
wherein the acoustic wave detector also serves as the acoustic wave transmitter.

4. The photoacoustic measurement device according to claim 2, further comprising:
an acoustic wave transmitter that performs transmission of the acoustic waves to the subject; and
a transmission circuit that outputs a transmission signal for causing the acoustic wave transmitter to transmit the acoustic waves from the acoustic wave detector,
wherein the acoustic wave detector also serves as the acoustic wave transmitter.

5. The photoacoustic measurement device according to claim 3,
wherein the probe further includes a transmission and reception changeover switch that switches a connection destination of the acoustic wave detector between the preamplifier and the transmission circuit, and
the controller further controls the transmission and reception changeover switch to cause the connection destination of the acoustic wave detector to be the preamplifier in a case where the photoacoustic waves are detected, the connection destination of the acoustic wave detector to be the selection switch in a case where the reflected acoustic waves are detected, and the connection destination of the acoustic wave detector to be the transmission circuit in a case where transmission of the acoustic waves is performed.

6. The photoacoustic measurement device according to claim 4,
wherein the probe further includes a transmission and reception changeover switch that switches a connection destination of the acoustic wave detector between the preamplifier and the transmission circuit, and
the controller further controls the transmission and reception changeover switch to cause the connection destination of the acoustic wave detector to be the preamplifier in a case where the photoacoustic waves are detected, the connection destination of the acoustic wave detector to be the selection switch in a case where the reflected acoustic waves are detected, and the connection destination of the acoustic wave detector to be the transmission circuit in a case where transmission of the acoustic waves is performed.

7. The photoacoustic measurement device according to claim 1,
wherein the probe further includes a first path changeover switch that switches a connection destination of a wire connected to the reception circuit between the selection switch and the preamplifier, and a second path changeover switch that switches a connection destination of a wire connected to the acoustic wave detector between the preamplifier and the selection switch, and
the controller further controls the first path changeover switch and the second path changeover switch to select the first path by connecting the wire connected to the reception circuit to the preamplifier using the first path changeover switch and connecting a wire connected to the acoustic wave detector to the preamplifier using the second path changeover switch in a case where the photoacoustic waves are detected, and select the second path by connecting the wire connected to the reception circuit to the selection switch using the first path changeover switch and connecting the wire connected to the acoustic wave detector to the selection switch using the second path changeover switch in a case where the reflected acoustic waves are detected.

8. The photoacoustic measurement device according to claim 7, further comprising:
an acoustic wave transmitter that performs transmission of the acoustic waves to the subject; and
a transmission circuit that outputs a transmission signal for causing the acoustic wave transmitter to transmit the acoustic waves from the acoustic wave transmitter,
wherein the acoustic wave detector also serves as the acoustic wave transmitter, the transmission circuit and the reception circuit are connected to the first path changeover switch via a common wire, and the first path changeover switch switches a connection destination of the common wire between the selection switch and the preamplifier, and in a case where transmission of the acoustic waves is performed, the controller also connects the common wire to the selection switch using the first path changeover switch, and connects a wire connected to the acoustic wave detector to the selection switch using the second path changeover switch.

9. The photoacoustic measurement device according to claim 1, wherein the probe further includes a first path changeover switch that switches a connection destination of a wire connected to the reception circuit between the selection switch and the preamplifier, the selection switch is arranged between a signal branching node provided between the acoustic wave detector and an input node of the preamplifier and the first path changeover switch, and the controller further controls the first path changeover switch to select the first path by connecting the wire connected to the reception circuit to the preamplifier using the first path changeover switch in a case where the photoacoustic waves are detected, and select the second path by connecting the wire connected to the reception circuit to the selection switch using the first path changeover switch in a case where the reflected acoustic waves are detected.

10. The photoacoustic measurement device according to claim 9, further comprising:

an acoustic wave transmitter that performs transmission of the acoustic waves to the subject; and a transmission circuit that outputs a transmission signal for causing the acoustic wave transmitter to transmit the acoustic waves from the acoustic wave transmitter, wherein the acoustic wave detector also serves as the acoustic wave transmitter, the transmission circuit and the reception circuit are connected to the first path changeover switch via a common wire, and the first path changeover switch switches a connection destination of the common wire between the selection switch and the preamplifier, and in a case where transmission of the acoustic waves is performed, the controller also connects the common wire to the selection switch using the first path changeover switch.

11. The photoacoustic measurement device according to claim 1, wherein the probe further includes a light emitting unit that emits the measurement light toward the subject.

12. The photoacoustic measurement device according to claim 1, wherein the controller controls an operation of the preamplifier by controlling power supply to the preamplifier.

13. The photoacoustic measurement device according to claim 12, wherein the controller causes the preamplifier to enter an operating state by supplying power to the preamplifier, and stops an amplification operation in the preamplifier by stopping the power supply to the preamplifier.

14. The photoacoustic measurement device according to claim 13, wherein the preamplifier includes an operational amplifier that amplifies and outputs the detection signal, and the controller stops the amplification operation in the preamplifier by stopping at least power supply to the operational amplifier.

15. The photoacoustic measurement device according to claim 1, wherein the preamplifier includes an operational amplifier that amplifies and outputs the detection signal, and a mode switching circuit that switches an operation mode between a first operation mode in which amplification of the detection signal is performed in the operational amplifier and a second operation mode in which at least the amplification of the detection signal is stopped in the operational amplifier, and the controller causes the mode switching circuit to select the first operation mode in a case where the photoacoustic waves are detected, and causes the mode switching circuit to select the second operation mode in the case where the reflected acoustic waves are detected.

16. A photoacoustic measurement method using a probe including an acoustic wave detector that detects photoacoustic waves generated by absorbing measurement light emitted toward a subject and reflected acoustic waves with respect to acoustic waves transmitted toward the subject and outputs a detection signal, and a preamplifier that amplifies the detection signal output by the acoustic wave detector, the method comprising:

causing the preamplifier to enter an operating state and selecting a first path along which the detection signal is amplified by the preamplifier and then is input to a reception circuit that receives the detection signal as a signal path between the acoustic wave detector and the reception circuit in a case where the photoacoustic waves are detected; and stopping an amplification operation in the preamplifier and selecting a second path along which the detection signal is input to the reception circuit without passing through the preamplifier as the signal path in a case where the reflected acoustic waves are detected.

* * * * *